(12) United States Patent
Buck

(10) Patent No.: US 11,969,544 B2
(45) Date of Patent: Apr. 30, 2024

(54) INHALERS AND AIRFLOW ADAPTORS THEREFOR

(71) Applicant: NORTON (WATERFORD) LIMITED, Waterford (IE)

(72) Inventor: Daniel Buck, Waterford (IE)

(73) Assignee: NORTON (WATERFORD) LIMITED, Waterford (IE)

( * ) Notice: Subject to any disclaimer, the term of this patent is extended or adjusted under 35 U.S.C. 154(b) by 583 days.

(21) Appl. No.: 16/476,390

(22) PCT Filed: Jan. 16, 2018

(86) PCT No.: PCT/EP2018/051036
§ 371 (c)(1),
(2) Date: Jul. 8, 2019

(87) PCT Pub. No.: WO2018/130727
PCT Pub. Date: Jul. 19, 2018

(65) Prior Publication Data
US 2020/0129711 A1    Apr. 30, 2020

(30) Foreign Application Priority Data
Jan. 16, 2017 (GB) .................................. 1700727.9

(51) Int. Cl.
*A61M 15/00* (2006.01)
*A61M 16/14* (2006.01)
(Continued)

(52) U.S. Cl.
CPC .... *A61M 15/0008* (2014.02); *A61M 15/0001* (2014.02); *A61M 15/0086* (2013.01);
(Continued)

(58) Field of Classification Search
CPC ........... A61M 15/0005–0008; A61M 15/0001; A61M 15/0086; A61M 15/0091;
(Continued)

(56) References Cited

U.S. PATENT DOCUMENTS

| 5,301,666 A * | 4/1994 | Lerk ................... A61M 15/002 |
| | | 128/203.15 |
| 2004/0069303 A1 | 4/2004 | Brown et al. |

(Continued)

FOREIGN PATENT DOCUMENTS

| WO | 2005025536 A2 | 3/2005 |
| WO | WO 2009-029027 A1 | 3/2009 |

(Continued)

OTHER PUBLICATIONS

Murphy, "Evaluation of Plume Geometry & Spray Pattern from a Dry Powder Devise using FDA Guidance", Dec. 2013 (Poster No. 21) Drug Delivery to the Lungs 24.

(Continued)

*Primary Examiner* — Elliot S Ruddie
(74) *Attorney, Agent, or Firm* — Morgan, Lewis & Bockius LLP

(57) ABSTRACT

The present disclosure describes an inhaler for the inhalation of powder medication. The inhaler has a body and at least one reservoir containing powder medication, the body having an air inlet and an outlet for the transmission to a patient of air entering the body through the air inlet and powder medication. The outlet has a total cross-sectional area for flow which is more than 80% of the total cross-sectional area of the air inlet.

19 Claims, 16 Drawing Sheets

(51) Int. Cl.
*G01N 15/00* (2006.01)
*G01N 15/06* (2006.01)

(52) U.S. Cl.
CPC ........ *A61M 15/0091* (2013.01); *A61M 16/14* (2013.01); *G01N 15/06* (2013.01); *A61M 2202/064* (2013.01); *G01N 2015/0046* (2013.01); *G01N 2015/0693* (2013.01)

(58) Field of Classification Search
CPC ............ A61M 16/14; A61M 2202/064; A61M 15/00; A61M 15/0065; A61M 15/002; A61M 15/0021; A61K 9/0075; A61K 31/137; A61K 31/56; A61K 31/58; A61P 11/00; A61P 11/06; G01N 15/06; G01N 2015/0046; G01N 2015/0693
USPC ........................................ 128/203.12, 203.15
See application file for complete search history.

(56) References Cited

U.S. PATENT DOCUMENTS

| | | |
|---|---|---|
| 2010/0000529 A1 | 1/2010 | Prime et al. |
| 2011/0108030 A1* | 5/2011 | Blair .................... A61K 9/0075 128/203.15 |
| 2012/0145150 A1 | 6/2012 | Donovan et al. |
| 2012/0280053 A1 | 11/2012 | Ortner et al. |
| 2014/0083424 A1 | 3/2014 | Hoekman et al. |

FOREIGN PATENT DOCUMENTS

| | | |
|---|---|---|
| WO | 2011054527 A1 | 5/2011 |
| WO | WO 2011-054529 A1 | 5/2011 |
| WO | WO 2012-078804 A1 | 6/2012 |

OTHER PUBLICATIONS

Murphy, "Understanding the affect of DPI device and lactose type on the output from a device", Dec. 2013 (Poster No. 48) Drug Delivery to the Lungs 24.

Murphy, "Evaluation of Dry Powder Device using High-speed Imaging Techniques", 2011, Drug Delivery to the Lungs 22.

"Envision Laser-Based Imaging System: Fully Characterises Nasal-And-Dry Powder-Based Systems", 2020, ONdrugDelivery Publishing, pp. 26-29.

Extended European Search Report, dated Mar. 28, 2023, for the corresponding European Patent Application No. 22213233.4, 11 pages.

Seamus DR et al.: "Understanding the affect of DPI device and lactose type on the output from a device", Drug Delivery to the Lungs, [Online] vol. 24, Dec. 11, 2013 (Dec. 11, 2013), XP055896242, Internet Retrieved from the Internet: URL:https://ddl-conference.com/wp-content/uploads/2016/09/48.Murphy.pdf> [retrieved on Mar. 1, 2022].

* cited by examiner

INHALERS AND AIRFLOW ADAPTORS THEREFOR

CROSS-REFERENCE TO RELATED APPLICATIONS

This application is the National Stage Entry under 35 U.S.C. § 371 of Patent Cooperation Treaty Application No. PCT/EP2018/051036, filed Jan. 16, 2018, the contents of which are hereby incorporated by reference herein.

FIELD OF THE INVENTION

The present invention relates to a dry powder inhaler. In particular, the present invention relates to a breath-actuated dry powder inhaler comprising an airflow adaptor. The invention also relates to methods of treating respiratory diseases of disorders.

BACKGROUND TO THE INVENTION

In the treatment of respiratory issues including asthma and COPD a problem is that patients have different levels of severity of disease. This severity can vary between patients and within the same patient on different days (good days and bad days). The most severe patients have difficulty producing a high flow rate when they inhale while the less severe patients may always have a high flow rate when they inhale. At present there is a one size fits all approach to inhaler development. The same device is used to administer medicine to all patients whether severe or mild. In order to treat the severe patients, the amount of active agent is increased. This does not address the variations in inhalation volume flow rate amongst a patient population and the effect that has on fine particle fraction delivery.

Deagglomerators for breath-actuated dry powder inhalers are disclosed in WO 01/97889.

EP 2496294-A discloses one type of inhaler with an air bypass.

There is, however, a continued need to reduce the flow rate dependence of breath-actuated dry powder inhalers and, in particular, the flow rate dependence of the delivered dose of the medicament they deliver. In particular, there is a need to ensure that different patient groups receive substantially the same delivered dose from the same breath-actuated dry powder inhaler.

There is also a need for providing breath-actuated dry powder inhalers, and in particular those with deagglomerators, which provide better delivered dose characteristics. Particularly, there is a need for breath-actuated dry powder inhalers which provide improved delivered dose uniformity.

These and other problems are addressed by a breath-actuated dry powder inhaler comprising an airflow adaptor; and a method for modifying airflow through the outlet port of a deagglomerator according to the independent claim. Further advantageous embodiments are disclosed in the dependent claims.

SUMMARY OF THE INVENTION

The present specification discloses an inhaler for the inhalation of powder medication, e.g. dry powder, the inhaler having a body and at least one reservoir containing powder medication, the body having an air inlet and an outlet for the transmission to a patient of air entering the body through the air inlet and dry powder medication, the outlet having a total cross-sectional area for flow which is more than 80% of the total cross-sectional area of the air inlet. This surprisingly and advantageously provides improved fine particle fraction consistency over the range of flow rates. This means that a severe patient will get a similar amount of medicine as would be delivered as a mild patient. Likewise a mild patient having a bad day, i.e. a low inhalation flow rate, would get the same amount as on a good day, i.e. a high inhalation flow rate. The relatively large outlet flow area, including bypass air, relative to inlet flow area would be expected to decrease in drug delivery at the lower flow rates. The addition of an airflow bypass would also be expected to create an unpredictable fine particle fraction delivery. Surprisingly, however, the flow rate dependency is in fact reduced.

The total cross-sectional area of the outlet maybe more than 85% of the total cross-sectional area of the inlet; optionally less than 125%, for example 90 to 100%, about 95% being one example. Arrangements within these values, especially at about 95%, have been found to provide particularly good fine particle fraction delivery across a wide range of flow rates, from 30 to 90 L/min or 45 to 90 L/min.

The outlet may comprise a primary outlet for the transmission of dry powder medicament entrained in air as well as at least one secondary outlet for the transmission of a bypass flow of air alone without medicament.

Each secondary outlet may be non-ring-like or non-annular in form.

Each secondary outlet may comprise a circular aperture.

A plurality of said secondary outlets maybe provided. In this case, said secondary outlets may be arranged in a series configured around the primary outlet. The series may comprise a rectangular grid of four circular apertures, although other arrangements are envisaged.

The primary outlet may be substantially circular.

The primary outlet may have a cross-sectional area of 30 to 50 mm$^2$, typically 35 to 45 mm$^2$, about 38.50 mm$^2$ being one example.

The total cross-sectional area of all said secondary outlets may be 5 to 15 mm$^2$, typically 8 to 12 mm$^2$, about 10.00 mm$^2$ being one example. Optionally, the cross-sectional areas of all said secondary outlets is about 10% to 50% of the area of the air inlet, typically 15% to 25%, about 20% being one example.

The total cross-sectional area of the air inlet may be 40 to 60 mm$^2$, typically 45 to 55 mm$^2$, about 50.80 mm$^2$ being one example.

The air inlet is generally elliptical in shape and may have at least an upper or lower edge portion thereof which is part of an ellipse; the air inlet preferably including at least one grille member extending thereacross parallel to a major axis of the generally elliptical shape of the air inlet.

The inhaler may include a deagglomerator which has a swirl chamber which includes at least one inlet port for air without powder medicament, as well as a medicament inlet for air with powder medicament, the area of flow through the at least one inlet port combined with the medicament inlet having a combined cross-sectional area which is less than the total cross-sectional area of the inlet to the body; preferably (a) also less than the cross-sectional area of the outlet and/or (b) about 40 mm$^2$.

The combined cross-sectional area may be 3 to 5 times larger than the total cross-sectional area of all said secondary outlets, for example about 4 times larger.

The outlet may be formed at a mouthpiece of the inhaler.

A cone angle of a plume of substance emitted by the inhaler may be less than 35 degrees. This cone angle may be more than 25 or more than 30 degrees, about 33.5 or 33.52 degrees being some examples. In any of these cases, the cone angle may be achieved with a pressure drop of 4 kPa applied at a mouthpiece of the inhaler to cause air to flow therethrough.

The cross sectional area at a distance 3 cm away from inhaler exit of a plume of substance emitted from the inhaler may be less than 6 cm$^2$, optionally less than 5 cm$^2$, for example about 4.5 cm$^2$. This cross sectional area, in any of these cases, may be more than 2 cm$^2$, more than 3 cm$^2$ or more than 4 cm$^2$. In any of these cases, the cross sectional area may in some examples be achieved with a pressure drop of 4 kPa applied at a mouthpiece of the inhaler to cause air to flow therethrough.

At a distance 3 cm away from inhaler exit the ratio of maximum to minimum cross-dimensions of a plume of substance emitted from the inhaler may be less than 1.8, optionally less than 1.7 or less than 1.6, 1.55 being one example. This ratio may in any of these cases be more than 1.2, more than 1.3, more than 1.4 or more than 1.5. In any of these cases, the ratio may in some examples be achieved with a pressure drop of 4 kPa applied at a mouthpiece of the inhaler to cause air to flow therethrough.

The exit plume may comprise a generally uniform spray pattern of powder particles across the plume, although the spray pattern may have denser spray near and at a centre of the plume than near or at a peripheral edge of the plume.

The inhaler may include dry powder medicament. This may include one or more active ingredients which may comprise a fluticasone propionate and salmeterol combination. The salmeterol may be salmeterol xinafoate. Other active ingredients are envisaged for other embodiments, as discussed below.

The primary and secondary ports may be configured such that delivery of Stage 4 particles in a Copley Scientific Next Generation Impactor test at pressure drops of 2 kPa, 4 kPa and 6 kPa varies between a most weight of particles and least weight of particles and the most weight of particles is less than 50% more than the least weight, optionally less than 35% more or less than 30% more, about 25% more being one example. The most weight may be more than 1%, more than 5% or more than 10% more than the least weight.

The primary and secondary ports may be configured such that delivery of Stage 5 particles in a Copley Scientific Next Generation Impactor test at pressure drops of 2 kPa, 4 kPa and 6 kPa varies between a most weight of particles and least weight of particles and the most weight of particles is less than 20% more than the least weight, optionally less than 17.5% more or less than 15% more, about 14% more being one example. The most weight may be more than 1%, more than 5% or more than 10% more than the least weight.

The present specification also discloses in another aspect an inhaler for the inhalation of powder medication, e.g. dry powder, the inhaler having a body and at least one reservoir containing powder medication, the body having an air inlet and an outlet for the transmission to a patient of air entering the body through the air inlet and powder medication, the outlet comprising a primary outlet for the transmission of dry powder medicament entrained in air as well as at least one secondary outlet for the transmission of a bypass flow of air, the primary and secondary outlets being configured to produce a plume of particulate substance emitted by the inhaler with a cone angle of the plume which is less than 35 degrees. This is optionally achieved at a pressure drop of 4 kPa applied across the inhaler.

The present specification discloses in another aspect an inhaler for the inhalation of powder medication, e.g. dry powder, the inhaler having a body and at least one reservoir containing powder medication, the body having an air inlet and an outlet for the transmission to a patient of air entering the body through the air inlet and powder medication, the outlet comprising a primary outlet for the transmission of dry powder medicament entrained in air as well as at least one secondary outlet for the transmission of a bypass flow of air, the primary and secondary outlets being configured to produce a plume of particulate substance emitted by the inhaler which at a plane 3 cm away from inhaler exit has a cross sectional area which is less than 6 cm$^2$. This is optionally achieved at a pressure drop of 4 kPa applied across the inhaler.

The present specification discloses in another aspect an inhaler for the inhalation of powder medication, e.g. dry powder, the inhaler having a body and at least one reservoir containing powder medication, the body having an air inlet and an outlet for the transmission to a patient of air entering the body through the air inlet and powder medication, the outlet comprising a primary outlet for the transmission of dry powder medicament entrained in air as well as at least one secondary outlet for the transmission of a bypass flow of air, the primary and secondary outlets being configured to produce a plume of particulate substance emitted from the inhaler which at a plane a distance 3 cm from inhaler exit has a ratio of maximum to minimum cross-dimensions which is less than 1.8. This is optionally achieved at a pressure drop of 4 kPa applied across the inhaler.

The present specification discloses in another aspect an inhaler for the inhalation of powder medication, the inhaler having a body, at least one reservoir containing powder medication and a swirl chamber for deagglomerating the powder medication, the body having an air inlet and an outlet for the transmission to a patient of air entering the body through the air inlet and powder medication, the outlet comprising a primary outlet for the transmission of dry powder medicament entrained in air as well as at least one secondary outlet for the transmission of a bypass flow of air, the primary and secondary outlets being configured to produce a plume of particulate substance emitted by the inhaler with a plume angle of from about 95 degrees to about 100 degrees. This is optionally achieved at a pressure drop of 4 kPa applied across the inhaler.

A further aspect of the invention provides a method of treating a respiratory disease or disorder comprising actuating the inhaler of any of the previous disclosures hereof to administer a therapeutically effective amount of one or more active ingredients.

The inhaler may be a dry powder inhaler and the step of actuating the inhaler may comprise inhaling through the inhaler.

The respiratory disease or disorder may be asthma.

The respiratory disease or disorder may be chronic obstructive pulmonary disease (COPD).

The one or more active ingredients may include budesonide and/or formoterol fumarate.

The one or more active ingredients may comprise albuterol or salbutamol sulphate.

The one or more active ingredients may comprise a fluticasone propionate and salmeterol combination. The salmeterol may be salmeterol xinafoate.

The one or more active ingredients may be provided in dry powder form. The dry powder may include a fluticasone propionate and salmeterol combination. The salmeterol may be salmeterol xinafoate. Other active ingredients may be used in other examples.

BRIEF DESCRIPTION OF THE FIGURES

The present invention may be carried out in various ways and a preferred disclosure will now be described by way of example with reference to the accompanying drawings, in which.

DETAILED DESCRIPTION

Figure 1:
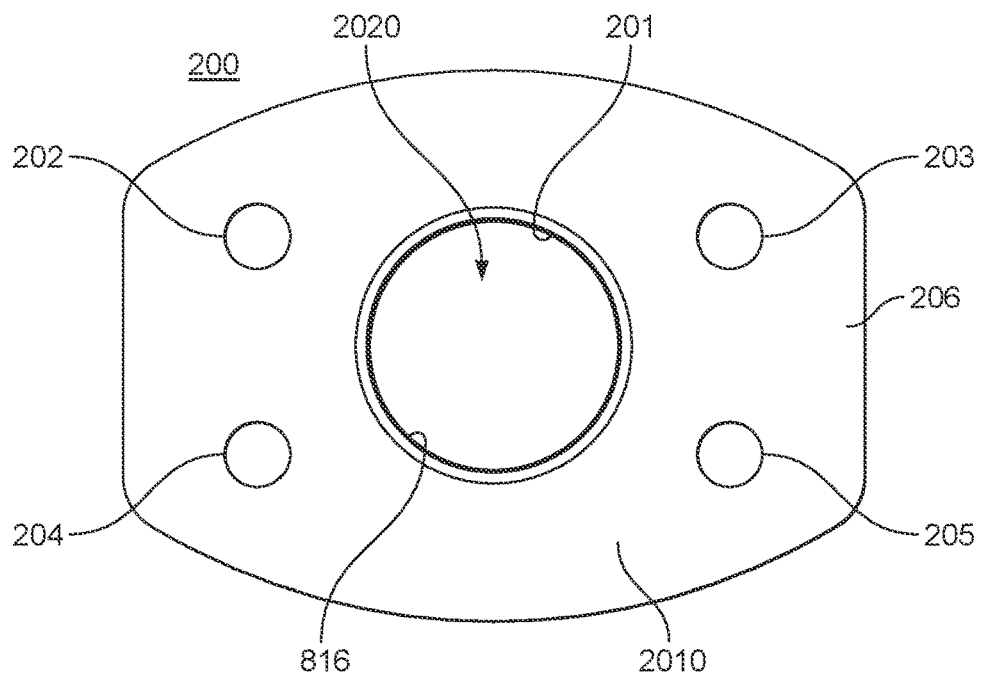
FIG. 1 shows a view of the distal end of an airflow adaptor used in a preferred inhaler.

FIG. 1 shows an embodiment of an airflow adaptor according to the present disclosure, in particular it shows a distal end 2010 of an airflow adaptor 200 for use in an inhaler. The airflow adaptor comprises a conduit 2020 with a first circumferential flange 206. The conduit 2020 has a circular cross-section; however, it may have any cross-sectional shape, for instance circular, square or triangular.

Figure 2:
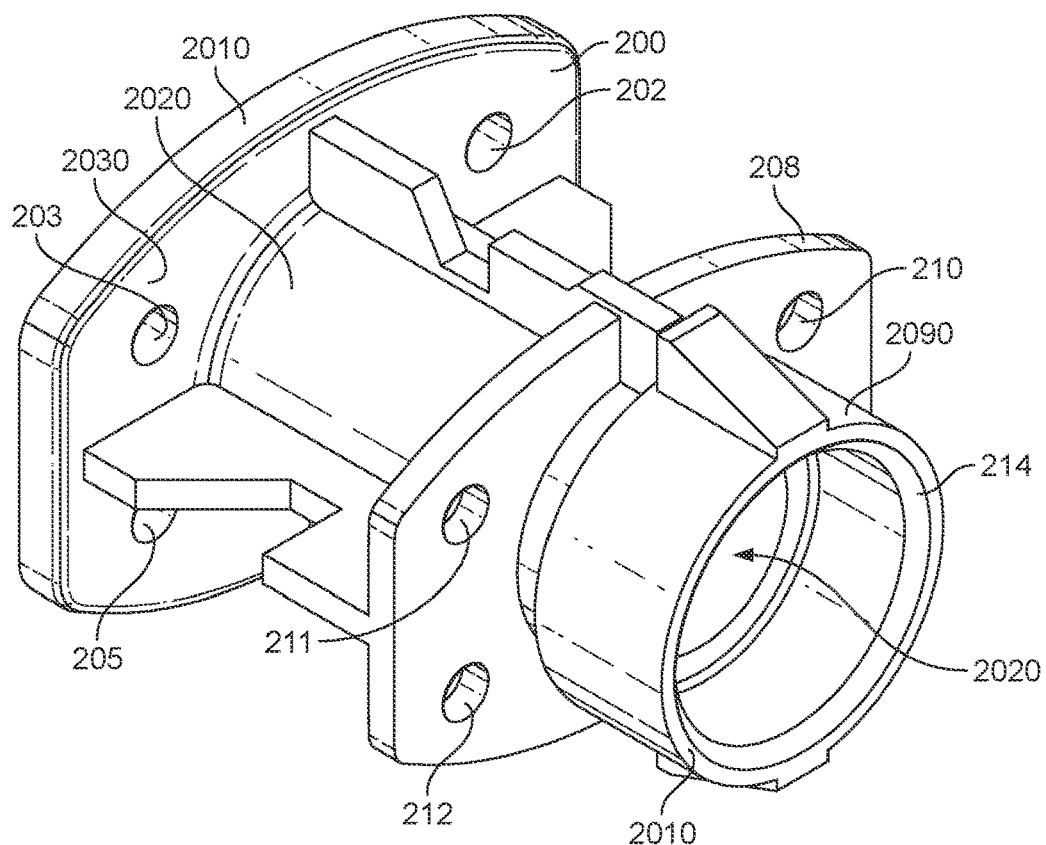
FIG. 2 shows a view of the proximal end of the airflow adaptor of FIG. 1.

FIG. 2 shows a view of the proximal end 2090 of the airflow adaptor 200. The airflow adaptor comprises a conduit 2020 with a first circumferential flange 2030. The conduit shown has a circular cross-section; however, it may have any cross-sectional shape, for instance circular, square or triangular.

The airflow adaptor 200 also comprises means for allowing air to flow from the proximal end 2090 of the adaptor to the distal end 2010 of the adaptor independently of the airflow in the conduit when a breath induced low pressure is applied to the distal end of the airflow adaptor 200. The means for allowing air to flow from the proximal end 2090 of the adaptor to a distal end 2010 of the adaptor independently of the airflow in the conduit 2020 when a breath induced low pressure is applied to the distal end 2010 of the airflow adaptor 200 are in the form of four apertures 202, 203, 204, 205 in the first circumferential flange 2030, which also has a relatively large circular central outlet 201.

In alternative embodiments there may be other numbers of apertures, for instance one, two, three, five, six, eight or more. The apertures shown have a circular cross-section; however, they may have any cross-sectional shape, for instance circular, square or triangular.

The airflow adaptor 200, as shown in FIG. 2, further comprises a second circumferential flange 208. The second circumferential flange comprises four apertures 210, 211, 212, (fourth not shown). The circumferential flange may, however, comprise any number of apertures, for instance one, two, three, four, six or eight apertures. The apertures shown have a circular cross-section; however, they may have any cross-sectional shape, for instance circular, square or triangular. The second circumferential flange 208 may be omitted in other embodiments.

The first and second circumferential flanges may be of any shape; however, they are preferably of a shape which enables them mate with the mouthpiece of a dry powder inhaler. Preferably, they mate such that during use air will not flow across the mating surface.

Figure 5:
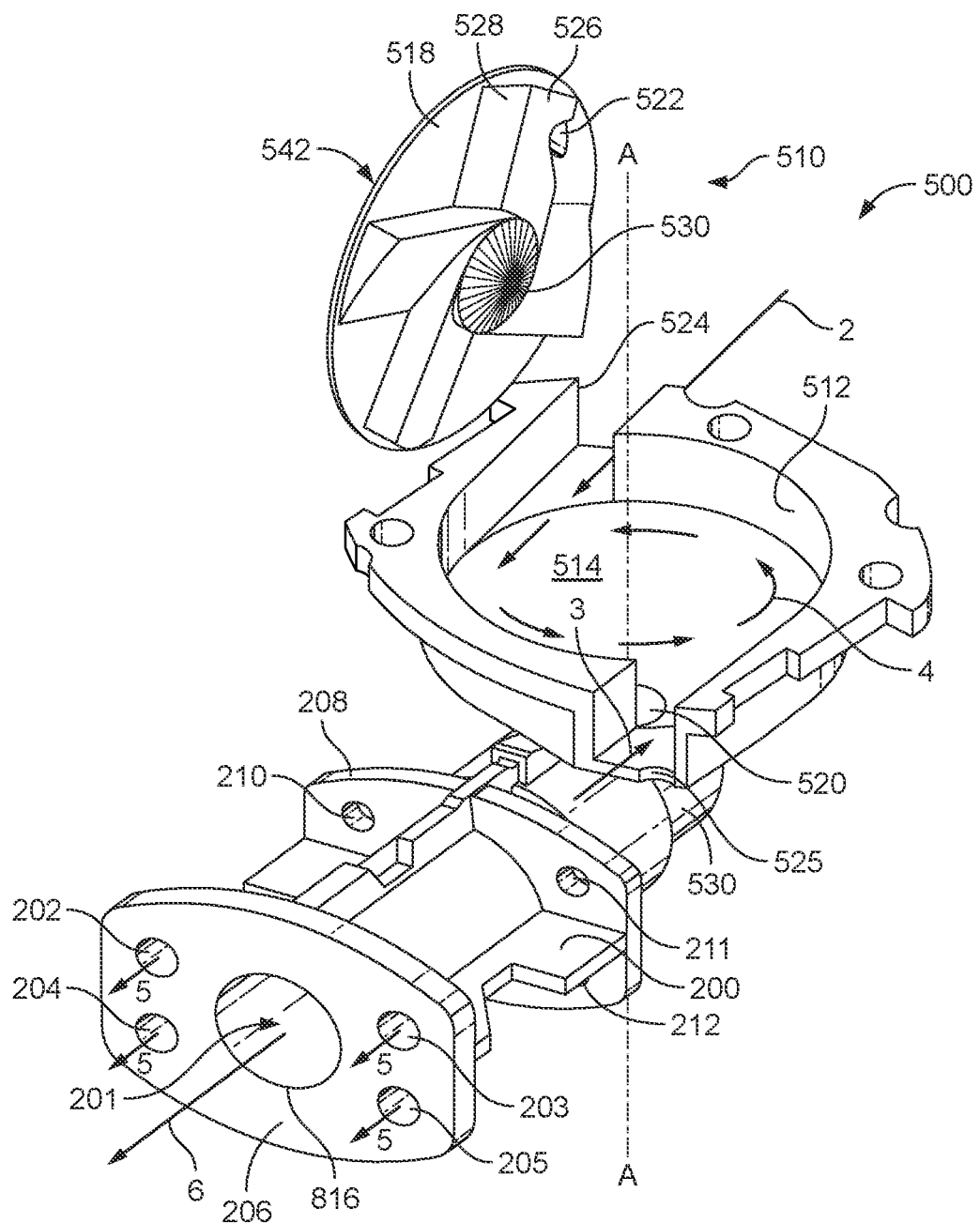
FIG. 5 shows the deagglomerator of FIG. 4 including a swirl chamber bypass port, the airflow adaptor being as in FIG. 2.

The proximal end 2090 of the adapter at conduit 2020 allows fluid communication from a deagglomerator outlet port 532 to the distal end of the conduit 2010. In particular, the airflow adaptor 200, as shown in FIG. 2, has a mating surface 214 for mating with the outlet port 532 of a deagglomerator 500 (FIG. 5). Preferably, they mate such that during use air will not flow across the mating surface. It is understood that in certain embodiments, the outlet port and the airflow adaptor may be a unitary structure.

Figure 3:
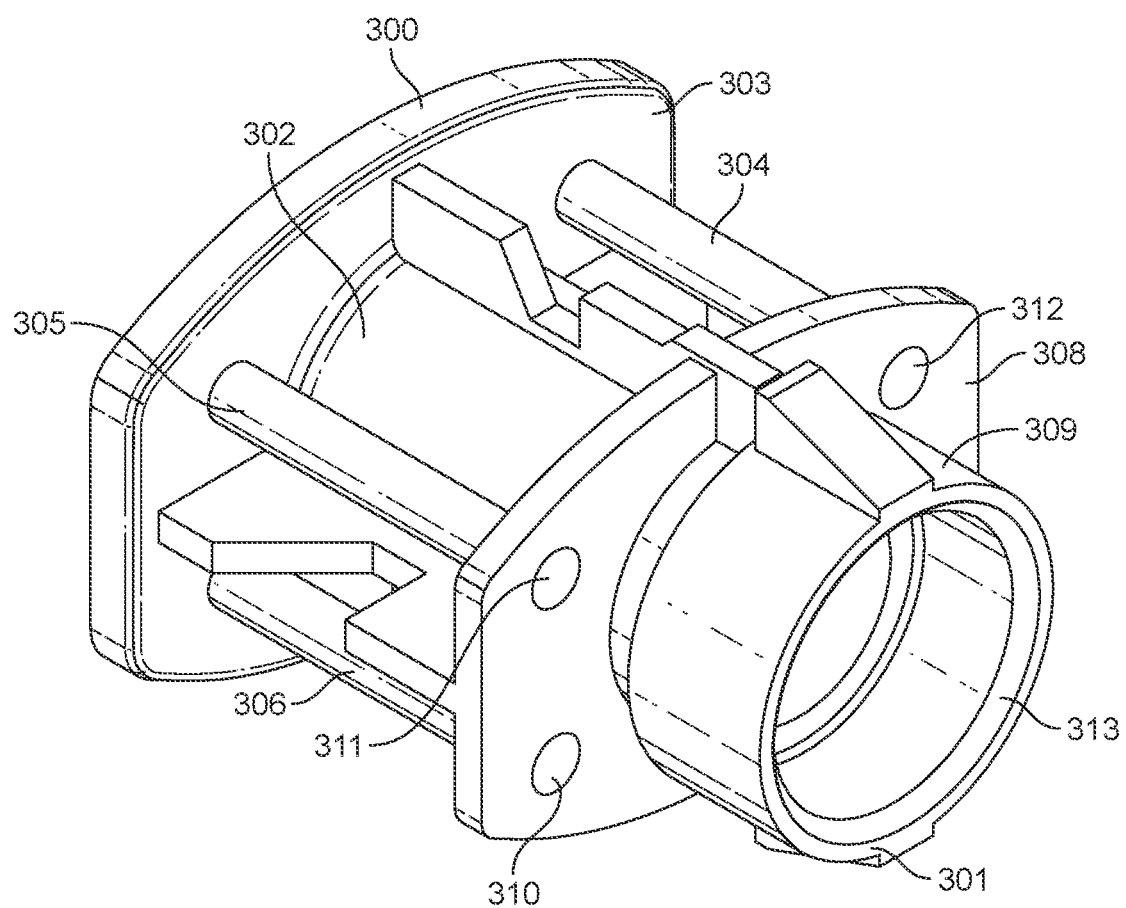
FIG. 3 shows an alternative embodiment of the airflow adaptor.

FIG. 3 shows a view of the proximal end 301 of a modified airflow adaptor 300. The airflow adaptor comprises a conduit 302 with a first circumferential flange 303. The conduit shown has a circular cross-section; however, it may have any cross-sectional shape, for instance circular, square or triangular.

The airflow adaptor 300 also comprises means for allowing air to flow from a proximal end of the adaptor to a distal end of the adaptor independently of the airflow in the conduit when a breath induced low pressure is applied to the distal end of the airflow adaptor 304, 305, 306 (fourth not shown). The means for allowing air to flow from a proximal end of the adaptor to a distal end of the adaptor independently of the airflow in the conduit when a breath induced low pressure is applied to the distal end of the airflow adaptor are in the form of four second conduits 304, 305, 306 (fourth not shown) running from the second circumferential flange 308 to the first circumferential flange 303. The second conduits shown have circular cross-sections 310, 311, 312 (fourth not shown); however, they may have any cross-sectional shape, for instance circular, square or triangular.

The proximal end 301 of the conduit 302 is suitable for making fluid communication with the outlet port of a deagglomerator of a dry powder inhaler. In particular, the airflow adaptor 300 shown in FIG. 3 has a mating surface 313 for mating with an outlet port of a deagglomerator of a dry powder inhaler. Preferably, they mate such that during use air will not flow across the mating surface. It is understood that in certain embodiments, the outlet port and the airflow adaptor may be a unitary structure.

The airflow adaptors of the present disclosure may be moulded from any suitable polymeric material. Suitable polymeric materials include polypropylene and acrylonitrile butadiene styrene (both available from BASF).

Figure 4:
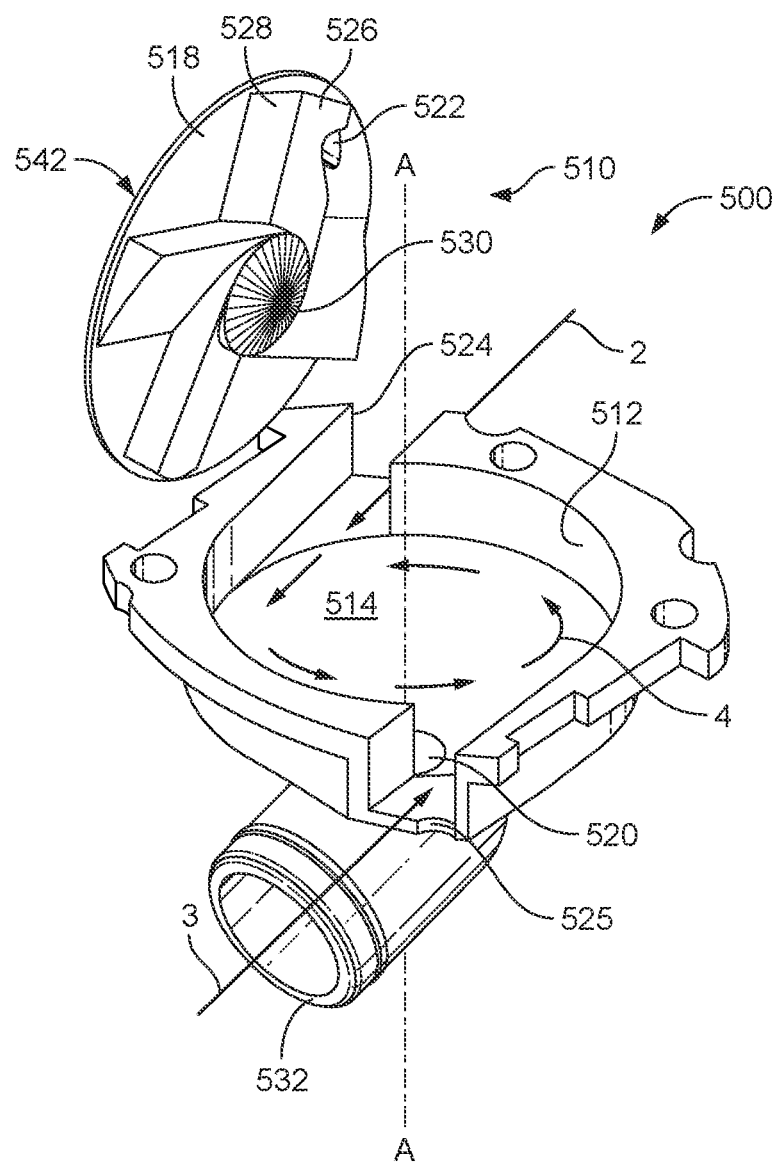
FIG. 4 shows a deagglomerator for use with airflow adaptor of FIG. 2, or as modified in FIG. 3.

FIG. 4 shows a deagglomerator 500 suitable for including the airflow adaptors of FIGS. 1 to 3. The deagglomerator 500 comprises: an inner wall 512 defining a swirl chamber 514 extending along an axis A from a first end 518 to a second end 520; a dry powder supply port 522 in the first end 518 of the swirl chamber 514 for providing fluid communication between a dry powder delivery passageway of an inhaler and the first end 518 of the swirl chamber 514; at least one inlet port 524, 525 in the inner wall 512 of the swirl chamber 514 adjacent to the first end 518 of the swirl chamber 514 providing fluid communication between a region exterior to the de-agglomerator 500 and the first end 518 of the swirl chamber 514; an outlet port 532 providing fluid communication between the second end 520 of the swirl chamber 514 and an airflow adaptor (not shown); whereby a breath induced low pressure at the distal end of the airflow adaptor (not shown) causes air to flow into the swirl chamber 514 through the dry powder supply port 522 and the inlet port 524, 525.

Preferably, the at least one inlet port 524, 525 comprises two diametrically opposed inlet ports 524, 525 that extend in a direction substantially transverse to the axis A and substantially tangential to the circular cross-section of the swirl chamber 514. As a result, airflows, illustrated by arrows 2 and 3 in FIG. 4, entering the swirl chamber 514 through the inlet ports are at least initially directed transverse with respect to the axis A of the swirl chamber and collide with the airflow entering through the supply port 522 to create turbulence. The combined airflows, illustrated by arrow 4 in FIG. 4, then collide with the inner wall 512 of the swirl chamber 514, form a vortex, and create additional turbulence as they move towards the second end 520 of the swirl chamber.

Referring to FIG. 4, the de-agglomerator 500 includes vanes 526 at the first end 518 of the swirl chamber 514 extending at least in part radially outwardly from the axis A of the swirl chamber. Each of the vanes 526 has an oblique surface 528 facing at least in part in a direction transverse to the axis A of the swirl chamber 514. The vanes 526 are sized such that at least a portion of the combined airflows 4 collide with the oblique surfaces 528. Preferably, the vanes comprise four vanes 526, each extending between a hub 530 aligned with the axis A and the wall 512 of the swirl chamber 514.

As shown in FIG. 4, the de-agglomerator 500 further includes an outlet port 532 for providing fluid communication between the second end 520 of the swirl chamber 514 and the airflow adaptor (not shown). A breath induced low pressure at the distal end of the airflow adaptor (not shown) causes the airflow through the supply port 522 and the airflows 2, 3 through the inlet ports and draws the combined airflow 4 through the swirl chamber 514. The combined airflow 4 then exits the swirl chamber 514 through the outlet port 532. Preferably the outlet port 532 extends substantially transverse to the axis A, such that the airflow 4 will collide with an inner wall of the outlet port 532 and create further turbulence.

During use of the de-agglomerator 500 in combination with a breath-actuated dry powder inhaler including a dry powder delivery passageway and a dry powder reservoir 800 (FIG. 7) for exposing a predetermined amount of dry powder to the delivery passageway, patient inhalation at the distal end 2010 of the airflow adaptor 200 causes airflows 2 and 3 to enter through, respectively, the dry powder supply port 522 and the inlet ports 524, 525. Although not shown, the airflow through the supply port 522 entrains the dry powder into the swirl chamber 514. The airflow and entrained dry powder are directed by the supply port 522 into the swirl chamber in a longitudinal direction, while the airflows 2 and 3 from the inlet ports 524, 525 are directed in a transverse direction, such that the airflows collide and substantially combine.

A portion of the combined airflow 4 and the entrained dry powder then collide with the oblique surfaces 528 of the vanes 526 causing particles and any agglomerates of the dry powder to impact against the oblique surfaces and collide with each other. The geometry of the swirl chamber 514 causes the combined airflow 4 and the entrained dry powder to follow a turbulent, spiral path, or vortex, through the swirl chamber. As will be appreciated, the decreasing cross-sections of the swirl chamber 514 continuously changes the direction and increases the velocity of the spiralling combined airflow 4 and entrained dry powder. Thus, particles and any agglomerates of the dry powder constantly impact against the wall 512 of the swirl chamber 514 and collide with each other, resulting in a mutual grinding or shattering action between the particles and agglomerates. In addition, particles and agglomerates deflected off the oblique surfaces 528 of the vanes 526 cause further impacts and collisions. The constant impacts and collisions cause any agglomerates to break into additional particles, and cause the particles to be substantially micronised.

Upon exiting the swirl chamber 514, the direction of the combined airflow 4 and the entrained dry powder is again changed to a transverse direction with respect to the axis A, through the outlet port 532. The combined airflow 4 and the entrained dry powder retain a swirl component of the flow, such that the airflow 4 and the entrained dry powder spirally swirls through the outlet port 532. Since the micronised powder and any remaining agglomerates maintain the swirl imparted from swirl chamber 514, the swirling flow causes additional impacts in the outlet port 532 so as to result in further breaking up of any remaining agglomerates prior to being inhaled by a patient.

FIG. 5 shows the deagglomerator 500 with the airflow adaptor 200 according to the invention. The deagglomerator 500 mates with the airflow adaptor 200 providing fluid communication between the outlet port 532 (FIG. 4) and a region exterior to the deagglomerator. The apertures 202, 203, 204, 205, 210, 211, 212 (fourth on second circumferential flange 208 (not shown)) act as swirl chamber by-pass ports which allow air to flow (shown by arrows labelled 5) from the proximal end 2090 (FIG. 2) of the airflow adaptor to the distal end 2010 (FIG. 2) of the airflow adaptor 200 independently of the swirl-chamber 514 when a breath-induced low pressure is applied to the distal end of the airflow adaptor. The breath induced low pressure at the distal end of the airflow adaptor 501 also causes air to flow into the swirl chamber 514 through the dry powder supply port 522 and the at least one inlet port 524, 525. The combined airflow (arrow 4) leaves the airflow adaptor 200 through the conduit of the central outlet 201 (shown by arrow 6). The airflow that has bypassed the swirl chamber leaves the airflow adapter through the apertures 202, 203, 204, 205 in the first circumferential flange 206 at a distal end 2010 (FIG. 1) of the airflow adaptor (shown by arrows numbered 5).

Suitable breath-actuated dry powder inhalers including the deagglomerators and airflow adaptors of the present invention are disclosed in U.S. Pat. No. 6,748,947 and are sold under the trade name SPIROMAX™.

Figure 6:
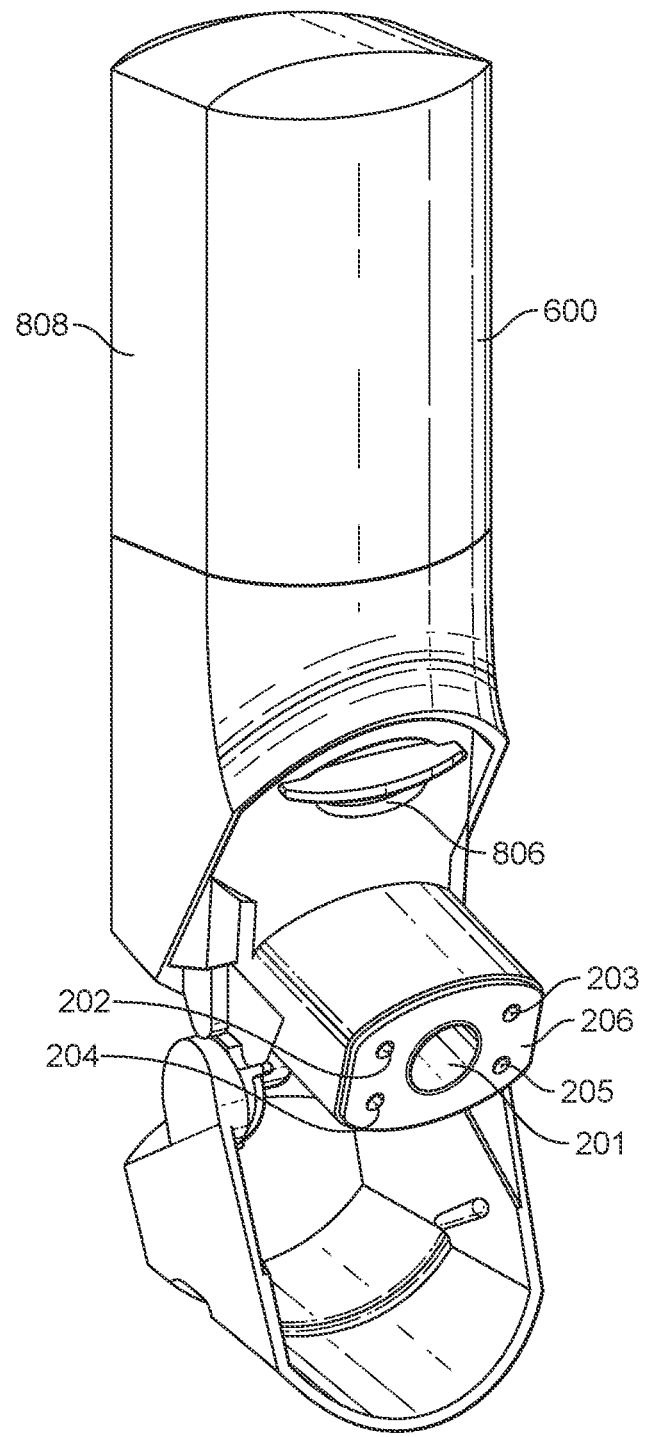
FIG. 6 shows a dry powder inhaler which includes the parts of FIGS. 4 and 5.

FIG. 6 shows the external appearance of a breath-actuated dry powder inhaler 600 to which the adaptor 200 and deagglomerator 500 are fitted.

Figure 7:
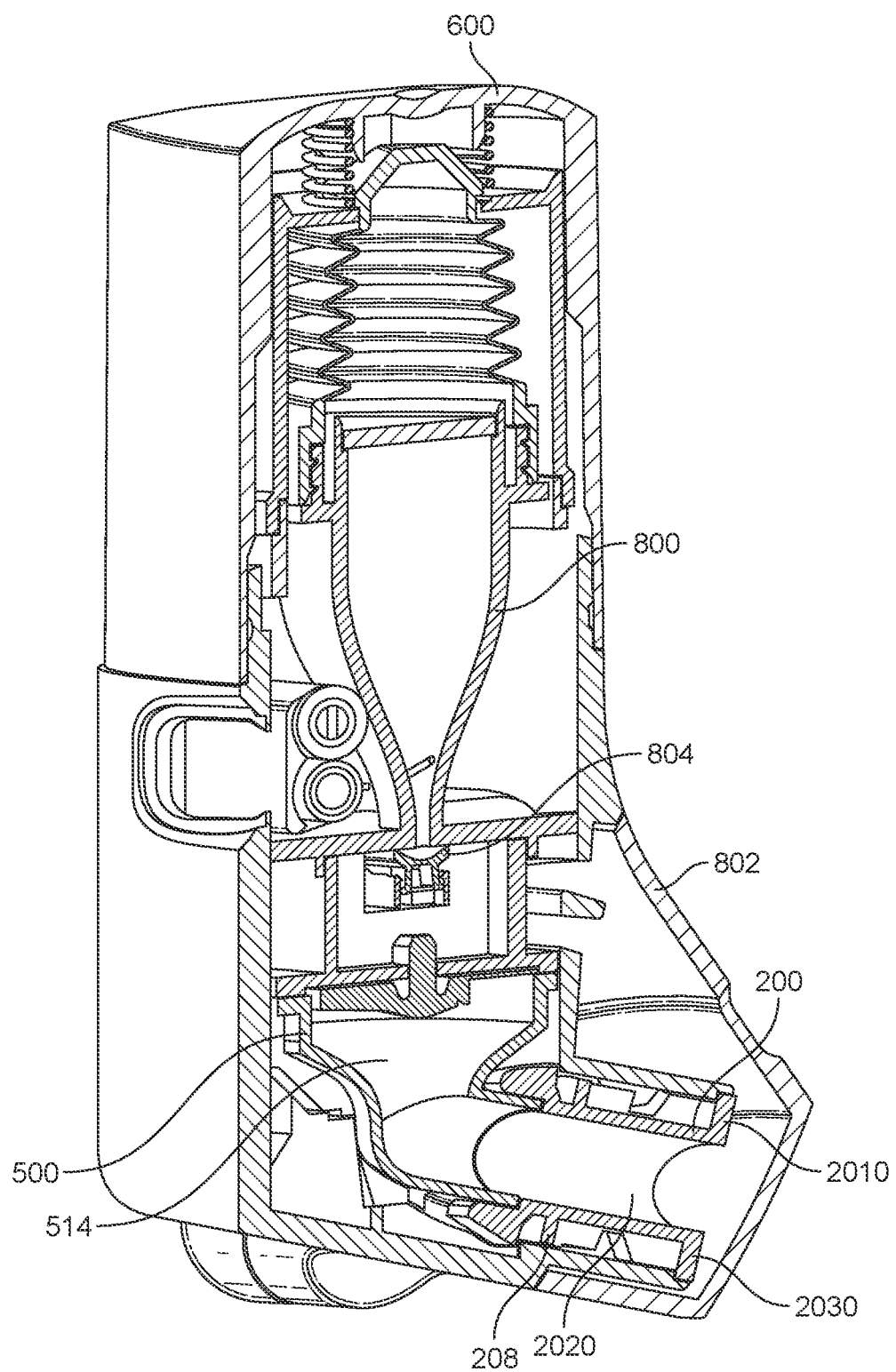
FIG. 7 shows a section through the dry powder inhaler of FIG. 6.

FIG. 7 shows in section the dry powder inhaler 600 comprising the deagglomerator 500 including an airflow adaptor 200.

The apertures 202, 203, 204, 205, 210, 211, 212 in the first and second circumferential flanges 2030, 208 perform the function of swirl chamber bypass ports. Accordingly, in use, a breath-actuated low pressure at the distal end 2010 of the airflow adaptor 200 causes air to flow through the apertures in the first 2030 and second 208 circumferential flanges. The breath-actuated low pressure at the distal end 2010 of the airflow adaptor 200 also causes air to entrain medicament and deliver it to the swirl chamber 514 via the supply port.

The vanes 526 are non-rotationally fixedly attached to the first end of the swirl chamber and extend at least in part radially outwardly from the axis A of the swirl chamber 514. The oblique surfaces 528 are such that a portion of the combined airflows is deflected in a substantially longitudinal direction towards the second end 520 of the swirl chamber 514.

Figure 8:
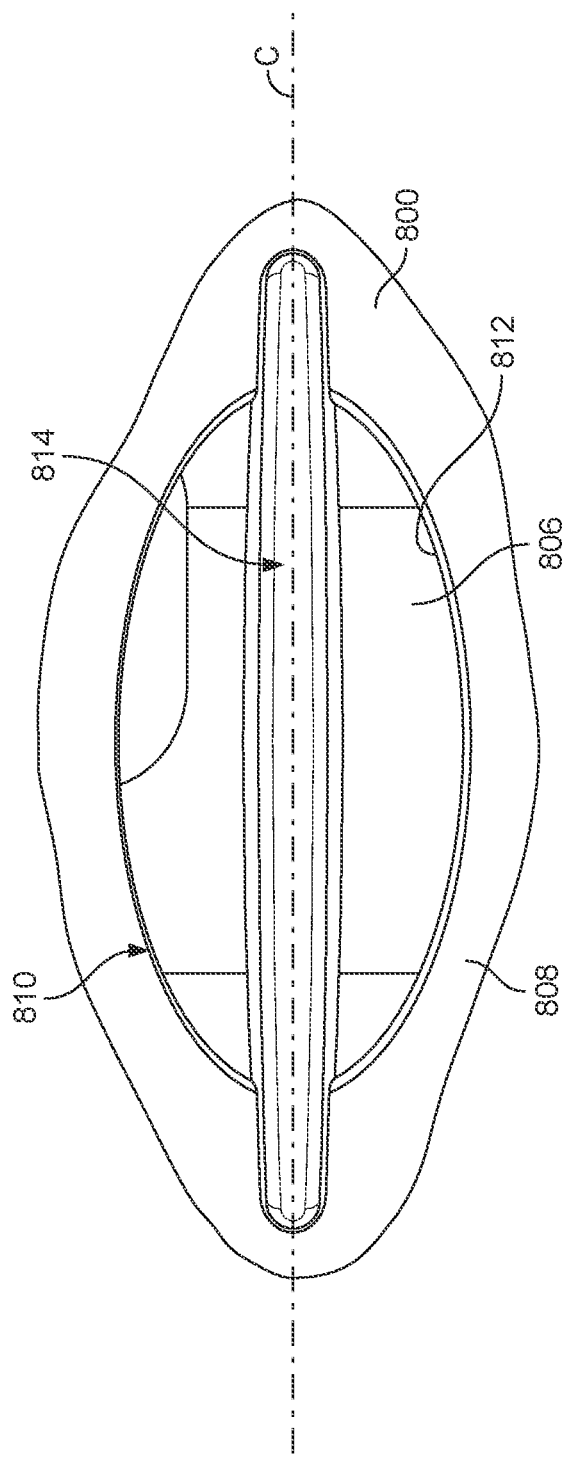
FIG. 8 shows the air inlet of the inhaler of FIGS. 6 and 7.

The inhaler has a mouthpiece cap 802 which is removable or rotatable for operatively moving a dosing cup 804 via a linkage (not shown) to fill the dosing cup 804 with dry powder medicament from the reservoir 800 and place the dosed dosing cup 804 in the dry powder delivery passageway which leads from an inhaler air inlet 806 (FIGS. 6 and 8) to the supply port 522 (FIG. 4).

The air inlet 806 is elliptical with its major axis C horizontal when a main body 808 of the inhaler is held vertical during inhalation. The air inlet 806 has an upper edge 810 and a lower edge 812 both of which are shaped to form part of an ellipse. The air inlet 806 has a central grille member 814 extending along its major axis C. The air inlet 806 has a cross-sectional area of 50.80 mm². The illustrated inlet 806 is the sole source of airflow to the outlet. The supply port 522, the air bypass port(s), the inlet ports 524, 525, and the outlet port, each share the same inlet 806.

The cross-sectional area of the supply port 522 is about 5 to 15 mm², about 7.5 mm² being one example.

Each of the two inlet ports 524, 525 has an area of about 10 to 20 mm², about 15 or about 16 mm² being two examples, so a total area between them of about 20 to 40 mm², about 30 or about 32 mm² being two examples. The cross-sectional area of the central circular outlet 816 of the conduit 2020 is 38.50 mm² and each of the bypass air apertures 202, 203, 204, 205 as well as each of the four apertures 210, 211, 212 in the second circumferential flange 208 is 2.5 mm², thus making a total outlet area of 48.50 mm², which is about 95% of the area of the air inlet 806. The outlet area is therefore relatively large being approximately equal to the inlet area. Furthermore, the bypass area of 10 mm² for all four apertures 202, 203, 204, 205 at the outlet is about 20% of the inlet area and about 25% of the area of the central outlet 816.

Figure 9:
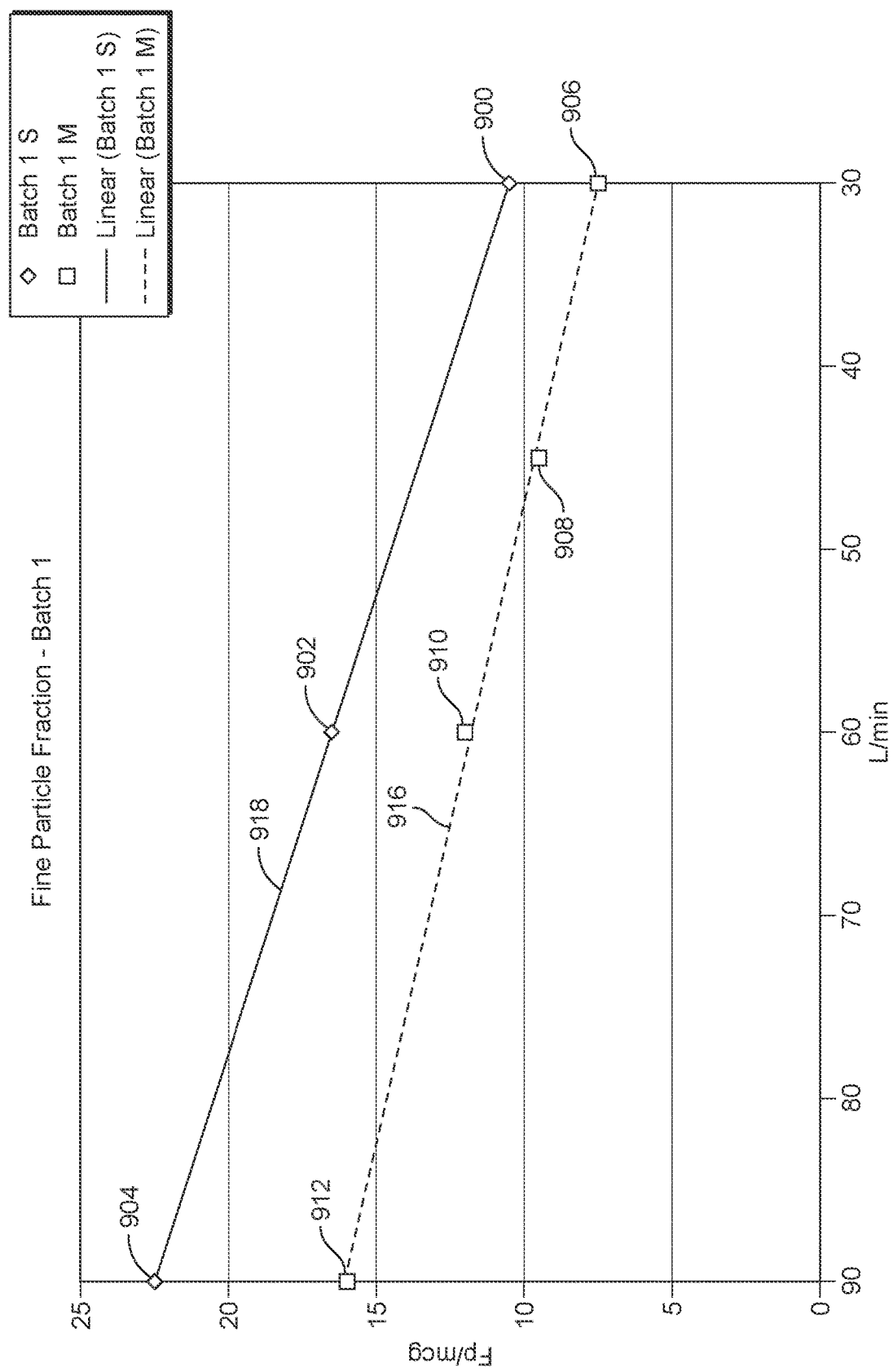
FIG. 9 shows comparative fine particle fraction graphs for a batch of dry powder medicine, one graph being for use with the inhaler of FIGS. 6 and 7 and the other the same but for the omission of the air bypass by having the bypass flow apertures omitted.
Figure 10:
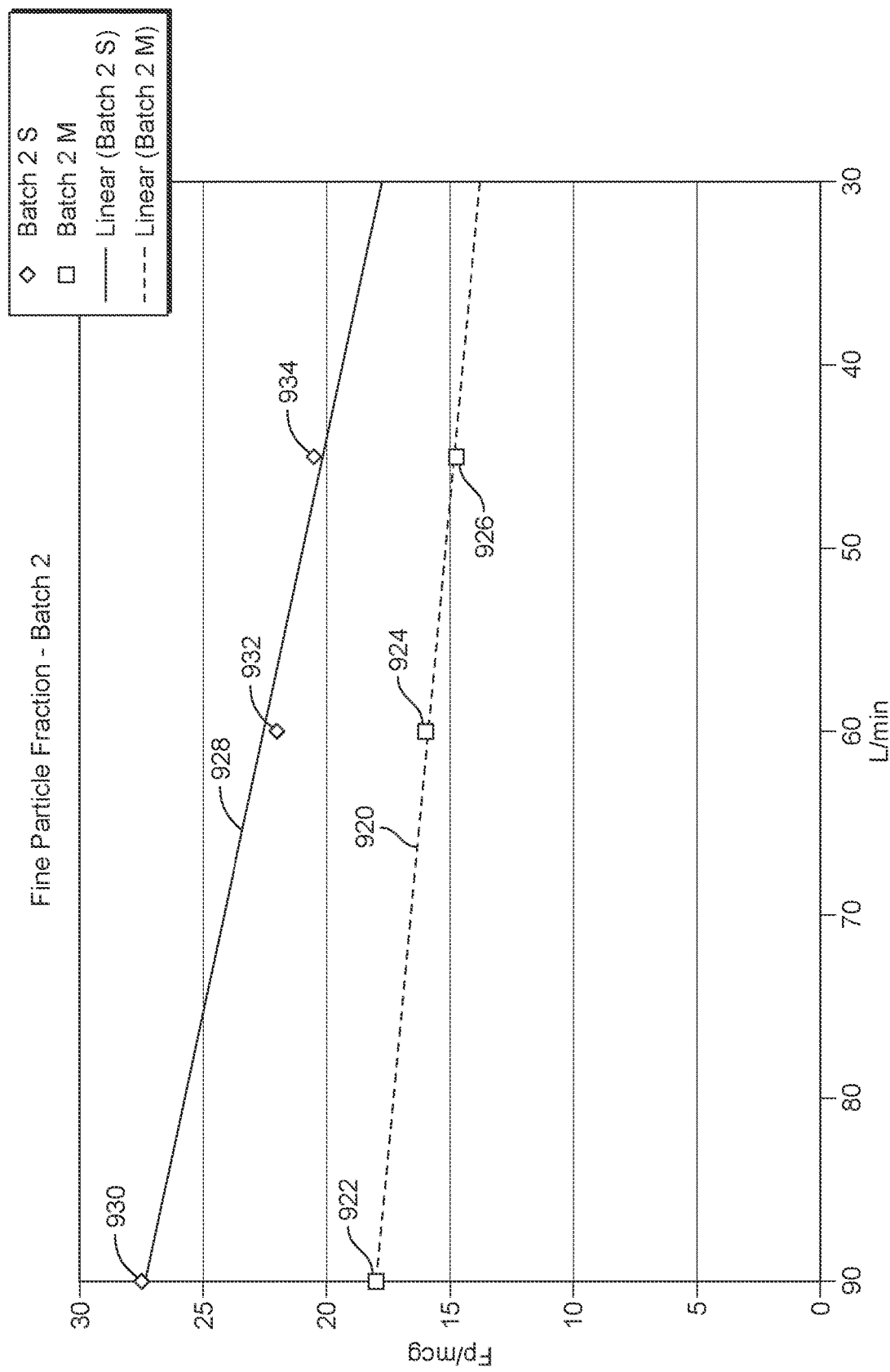
FIG. 10 shows graphs corresponding to those of FIG. 9 but for a second batch of dry powder medication.

These arrangements have significant advantages as shown by FIGS. 9 and 10.

In FIG. 9, Batch IS shows with diamond plots 900, 902, 904 the fine particle fraction (measured using a Copley Scientific NGI tester as described in "Copley Scientific—Quality Solutions for Inhaler Testing—2012 Edition"), i.e. Groups 3 or 4 (Stages 3, 4, 5, 6, 7, MOC) delivered at different volume flow rates by an inhaler as shown but with apertures 202, 203, 204, 205 omitted as well as second circumferential flange 208. Batch IM shows with square plots 906, 908, 910, 912 the equivalent data for the inhaler 600 presently disclosed. It is a great surprise that due to the introduction of the bypass air and the relatively large outlet area compared to inlet area of the inhaler 600 there isn't a poor drop off in low flow rate performance with the inhaler 600. On the contrary, the shallower gradient of the square plots 906, 908, 910, 912 compared to the plots 900, 902, 904 shows greatly improved performance in that there is a significantly more consistent delivery of fine particle fraction over the range of volume flow rates, as shown by flatter linear line 916 for the square plots compared to steeper line 91 for diamond plots. Likewise, in FIG. 10, with a second batch, linearised line 920 for square plots 922, 924, 926 with inhaler 600 is significantly flatter than linearised line 928 for diamond plots 930, 932, 934 for the inhaler with no air bypass.

Comparative Test

Inhaler mouthpieces as in FIGS. 6 and 7 (known as a "high flow device") were tested against mouthpieces the same but for the absence of the bypass flow path through the bypass apertures 202, 203, 204, 205, 210, 211, 212 (known as a standard device). The devices were tested with the Copley Scientific Next Generation Impactor (NGI) tester, as described in "Copley Scientific—Quality Solutions for Inhaler Testing—2012 Edition" using albuterol as the active ingredient.

The NGI A tests were made at the following three pressure settings using the NGI tester:

| Pressure Drop | Standard Flow Devices | High Flow Devices |
| --- | --- | --- |
| 2 kPa | 1 device | 1 device |
| 4 kPa | 1 device | 1 device |
| 6 kPa | 1 device | 1 device |

NGI A Tests at 3 different Pressure Drop settings:

| Flow Rate | High Flow Devices |
| --- | --- |
| Low Flow rate from 2 kPa Std. Flow test above | 1 device |
| Medium Flow rate from 4 kPa Std. Flow test above | 1 device |
| High Flow rate from 6 kPa Std. Flow test above | 1 device |

The materials used were:

Albuterol MDPI 90 mcg/dose 200 doses (Salbutamol Sulphate), 0.65 g fill weight, priming 50 l/min..

The devices were wasted at the same flow rate that the testing was performed at.

The results were as follows in Table 1 below:

TABLE 2

| TEST | INHALER NUMBER | PARAMETER (UNITS) | 2 KPa | | | 4 KPa | | | 6 KPa | | |
| --- | --- | --- | --- | --- | --- | --- | --- | --- | --- | --- | --- |
| | | | Standard Inhaler @ 46 L/min | High Flow Inhaler @ 65 L/min | High Flow Inhaler @ 46 L/min | Standard Inhaler @ 67 L/min | High Flow Inhaler @ 92 L/min | High Flow Inhaler @ 67 L/min | Standard Inhaler @ 84 L/min | High Flow Inhaler @ 117 L/min | High Flow Inhaler @ 84 L/min |
| NEXT GEN- | Inhalers 1-3 | MP/P (mcg) Pre-Sep (mcg) | 15.25 37.24 | 5.29 50.27 | 7.81 51.38 | 10.31 35.44 | 5.9706 45.6166 | 4.4376 48.6701 | 8.5468 34.9633 | 6.4409 41.3343 | 4.5011 47.8467 |

TABLE 2-continued

| TEST | INHALER NUMBER | PARAMETER (UNITS) | 2 KPa | | | 4 KPa | | | 6 KPa High Flow | | |
|---|---|---|---|---|---|---|---|---|---|---|---|
| | | | Standard Inhaler @ 46 L/min | High Flow Inhaler @ 65 L/min | High Flow Inhaler @ 46 L/min | Standard Inhaler @ 67 L/min | High Flow Inhaler @ 92 L/min | High Flow Inhaler @ 67 L/min | Standard Inhaler @ 84 L/min | Inhaler @ 117 L/min | High Flow Inhaler @ 84 L/min |
| ERATION IM-PACTOR | #22-26 | Stage 1 (mcg) | 0.37 | 1.19 | 0.49 | 1.28 | 2.5615 | 1.4799 | 2.1202 | 3.5801 | 1.6608 |
| | | Stage 2 (mcg) | 0.58 | 1.25 | 0.82 | 1.16 | 2.95 | 1.1259 | 1.7529 | 4.4723 | 1.9029 |
| | | Stage 3 (mcg) | 2.33 | 4.36 | 2.56 | 4.55 | 7.5856 | 3.791 | 6.0295 | 9.0953 | 5.5148 |
| | | Stage 4 (mcg) | 10.91 | 11.85 | 10.57 | 14.61 | 13.3816 | 11.1413 | 16.4655 | 14.7192 | 12.7265 |
| | | Stage 5 (mcg) | 17.44 | 12.28 | 13.99 | 15.31 | 11.3786 | 11.386 | 14.4183 | 10.7872 | 11.1037 |
| | | Stage 6 (mcg) | 9.58 | 4.89 | 5.76 | 8.75 | 5.5966 | 5.3054 | 8.4375 | 4.7022 | 4.5773 |
| | | Stage 7 (mcg) | 2.74 | 1.36 | 1.69 | 2.66 | 2.5954 | 1.398 | 2.5336 | 1.9779 | 1.2455 |
| | | Stage MOC (mcg) | 0.70 | 0.29 | 0.58 | 0.72 | 1.0738 | 0.3035 | 0.5688 | 0.5348 | 0.2694 |
| | | Total Drug Recovery (mcg) | 97.16 | 93.04 | 95.66 | 94.79 | 96.7193 | 89.0387 | 96.9364 | 97.6442 | 91.3497 |
| | | Mass Balance (%) | 106 | 103 | 106 | 105.00 | 110 | 99 | 107 | 108 | 101 |
| | | Group 1 (MP/P, Pre-Sep) (mcg) | 52 | 56 | 59 | 46.00 | 52 | 53 | 44 | 48 | 52 |
| | | Group 2 (Stage 12) (mcg) | 1 | 2 | 1 | 2.00 | 6 | 3 | 4 | 8 | 4 |
| | | Group 3 (Stage 3, 4, 5) (mcg) | 31 | 28 | 27 | 34.00 | 32.0 | 26 | 37 | 35 | 29 |
| | | Group 4 (Stage 6, 7 MOC) (mcg) | 13 | 7 | 8 | 12.00 | 9.0 | 7 | 12 | 7 | 6 |

Figure 11A:
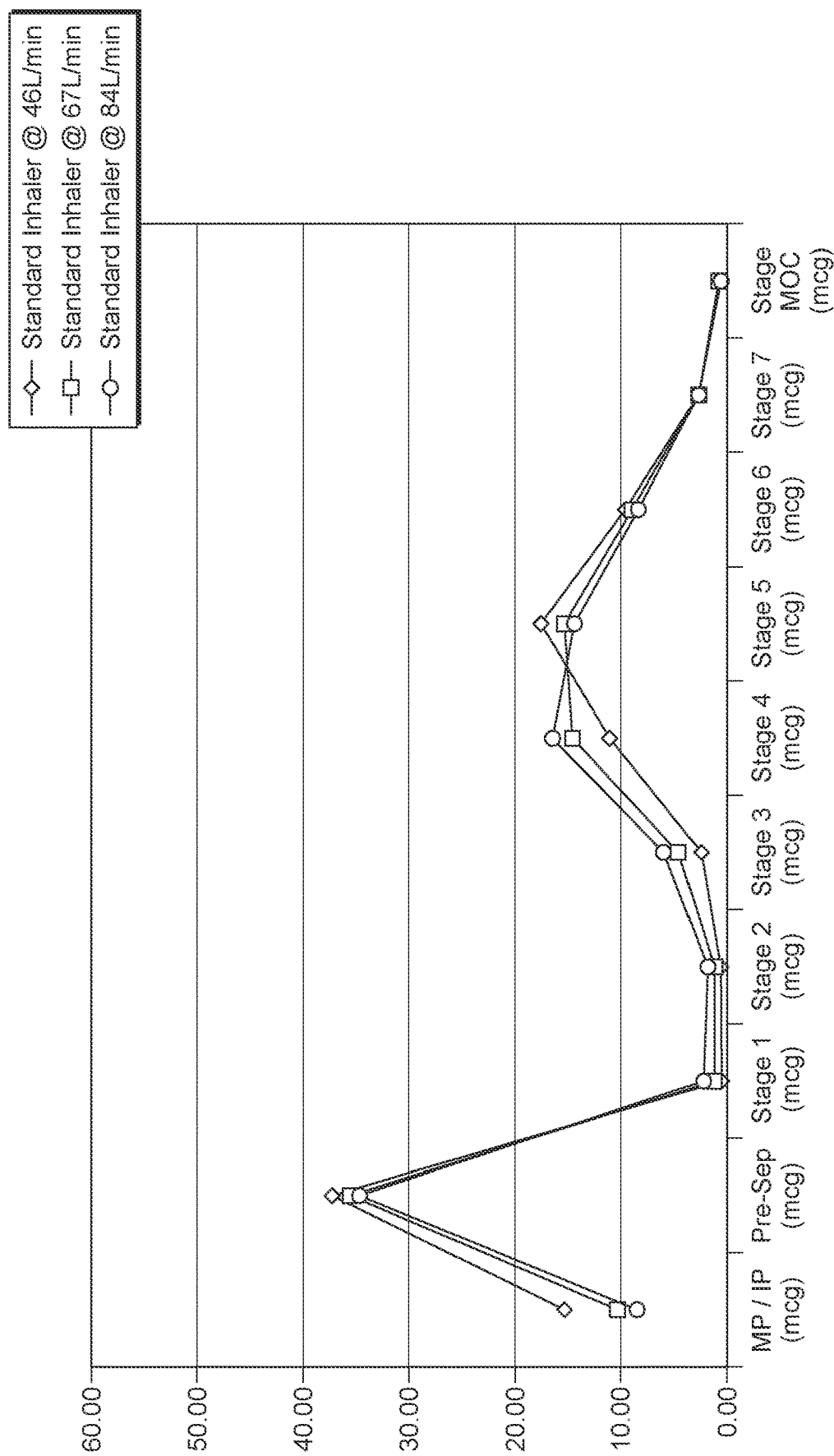
FIG. 11A to 11C show graphs corresponding to the results in Table 1.
Figure 11B:
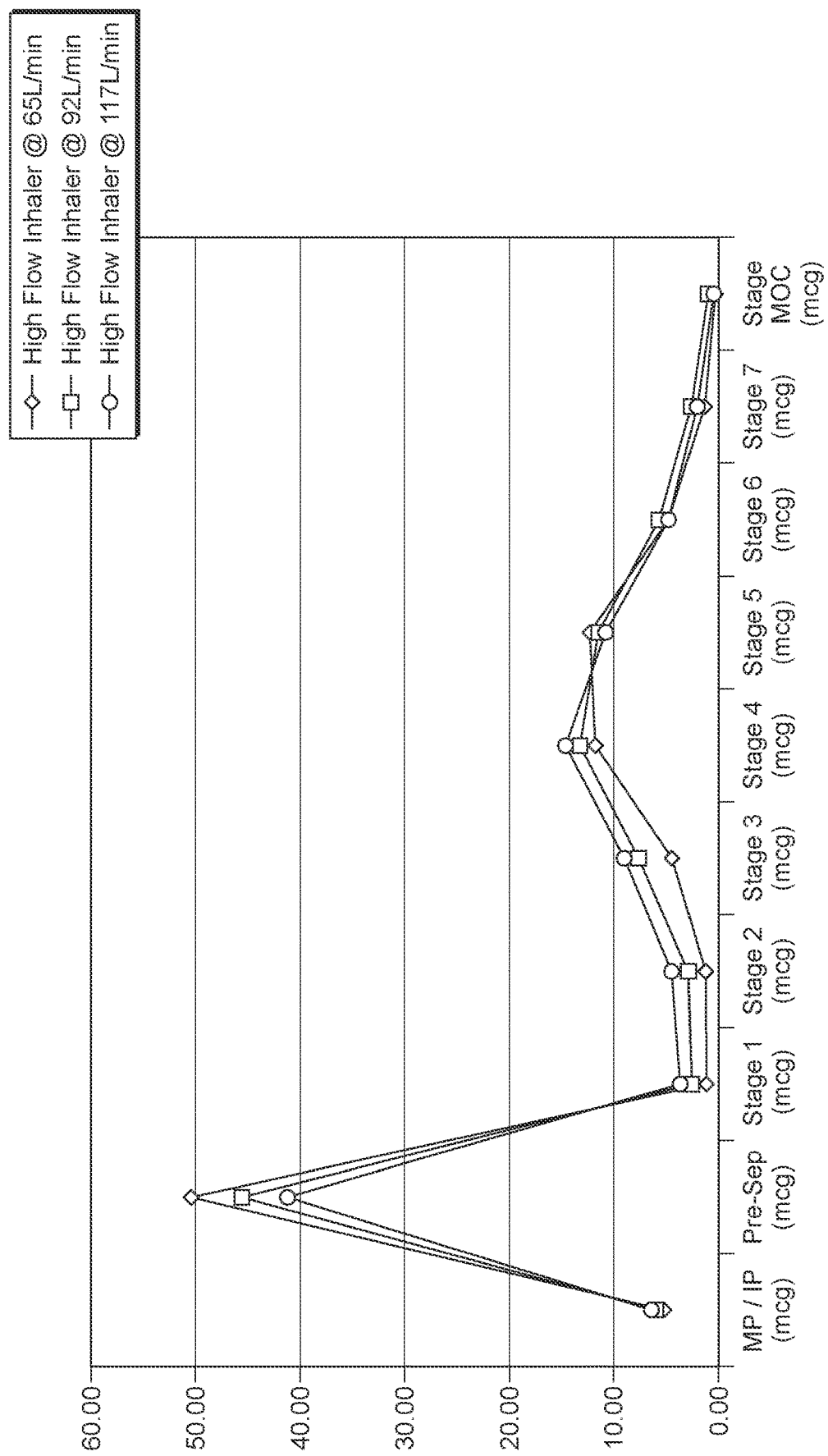
Figure 11C:
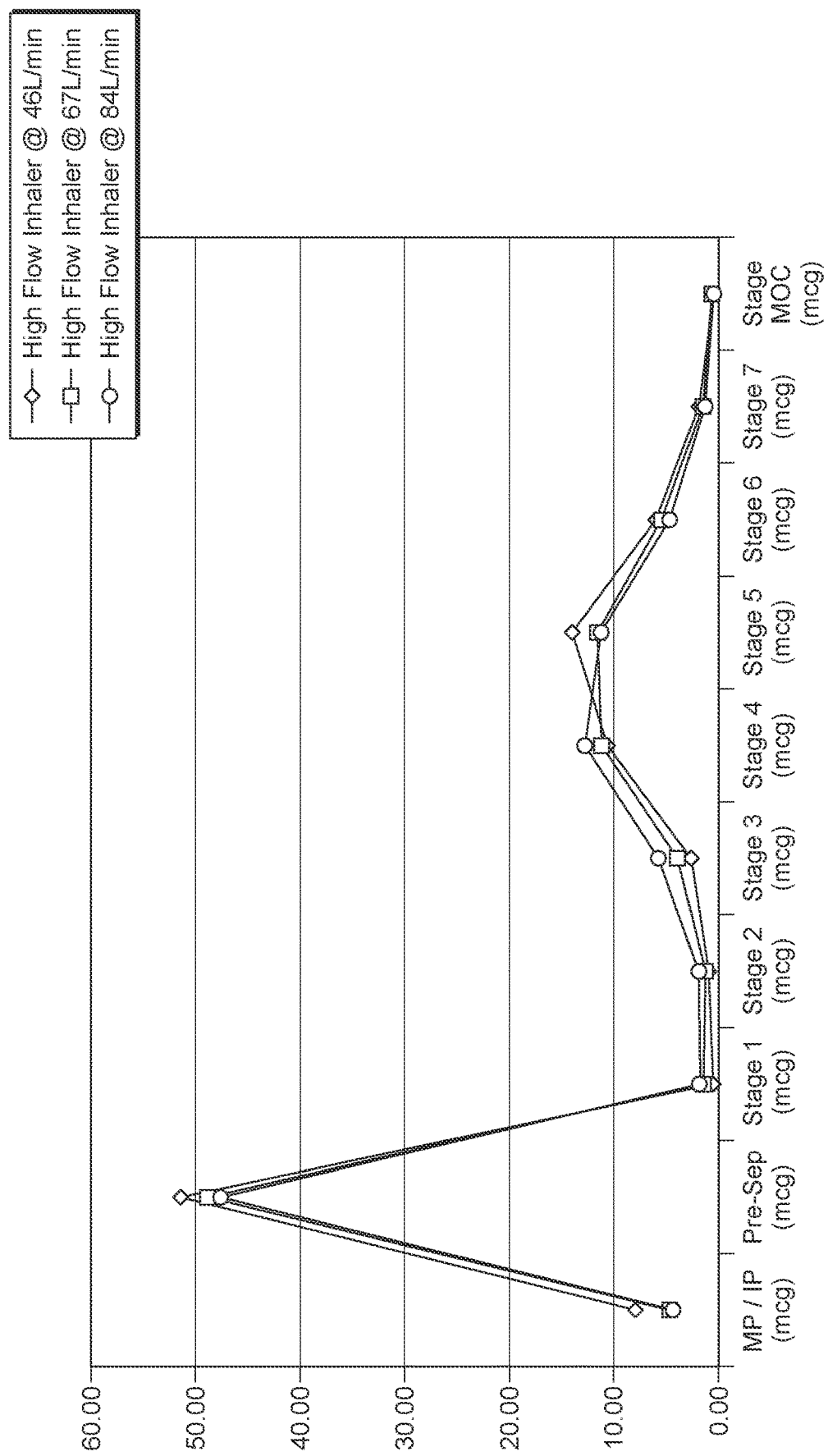
Figure 12A:
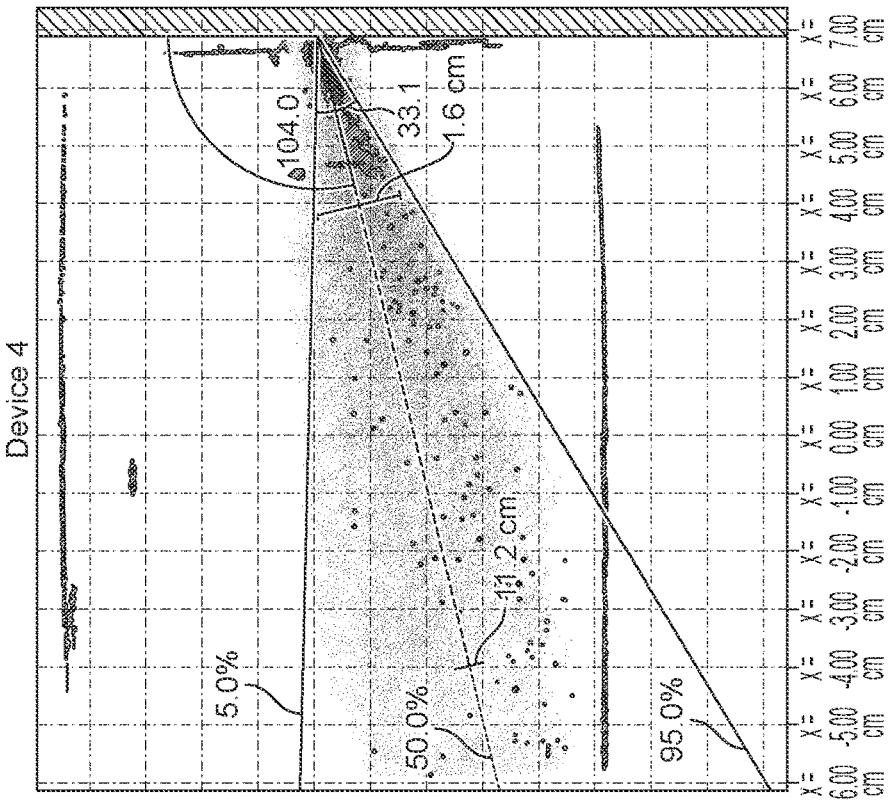
FIG. 12A and 12B show the results of plume cone angle testing.
Figure 12A:
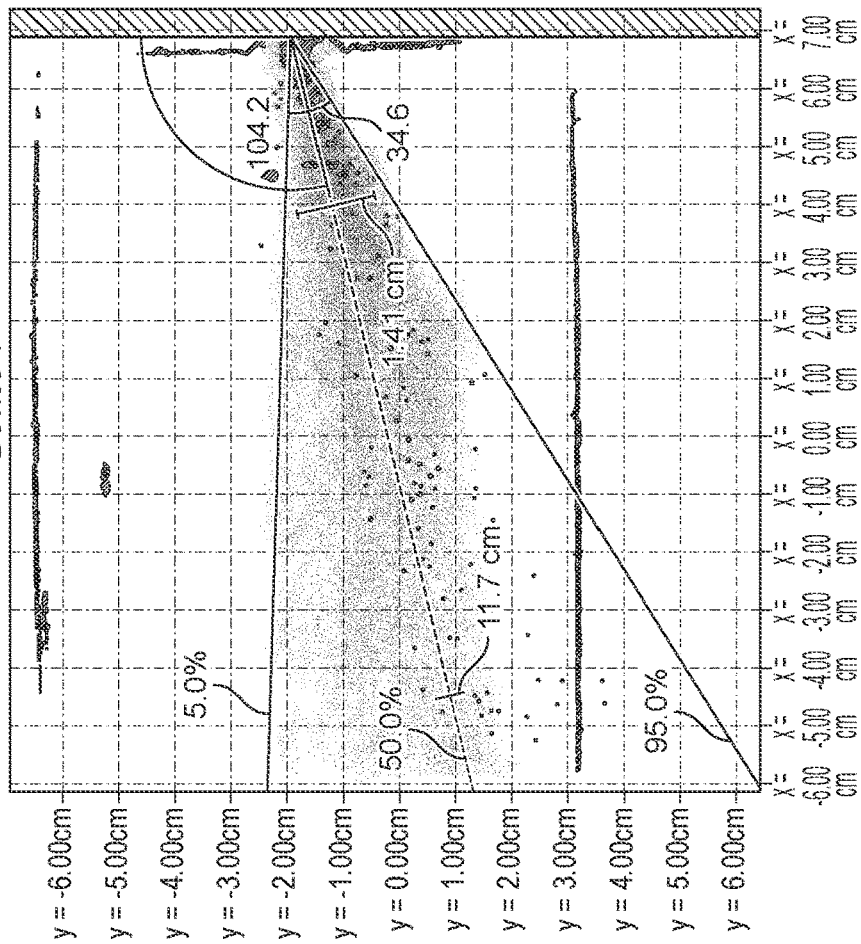
Figure 12B:
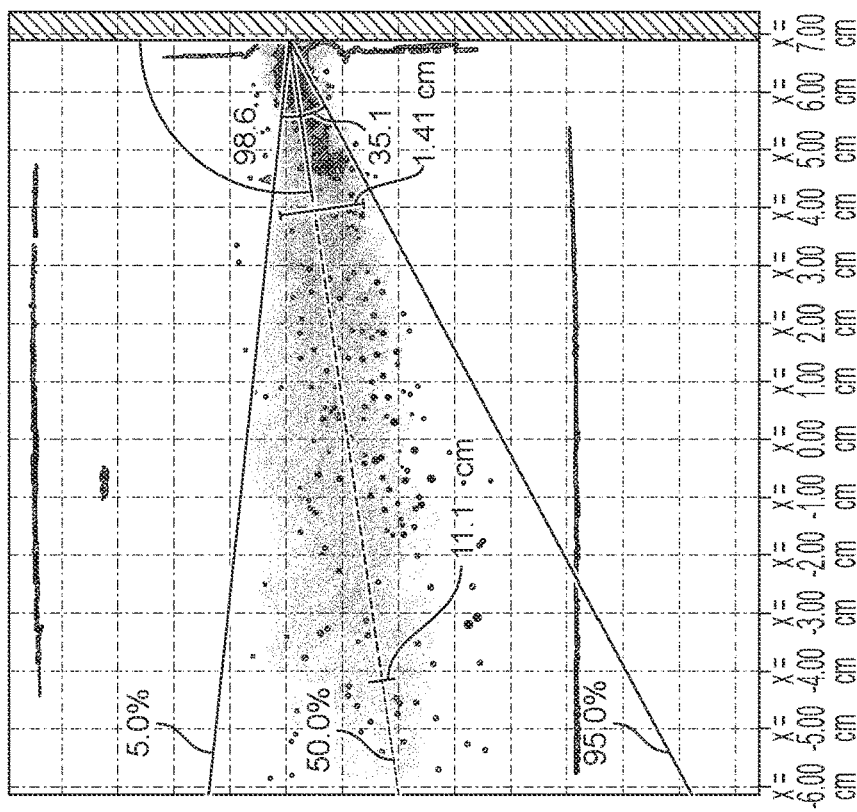
Figure 12B:
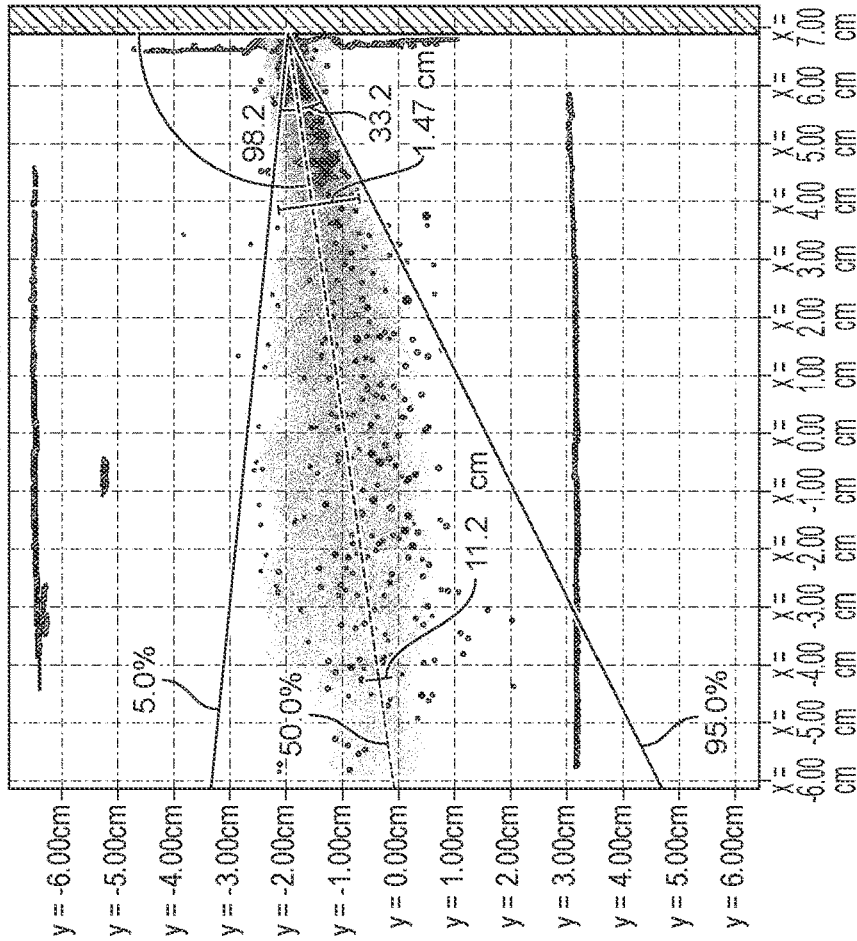
Figure 13A:
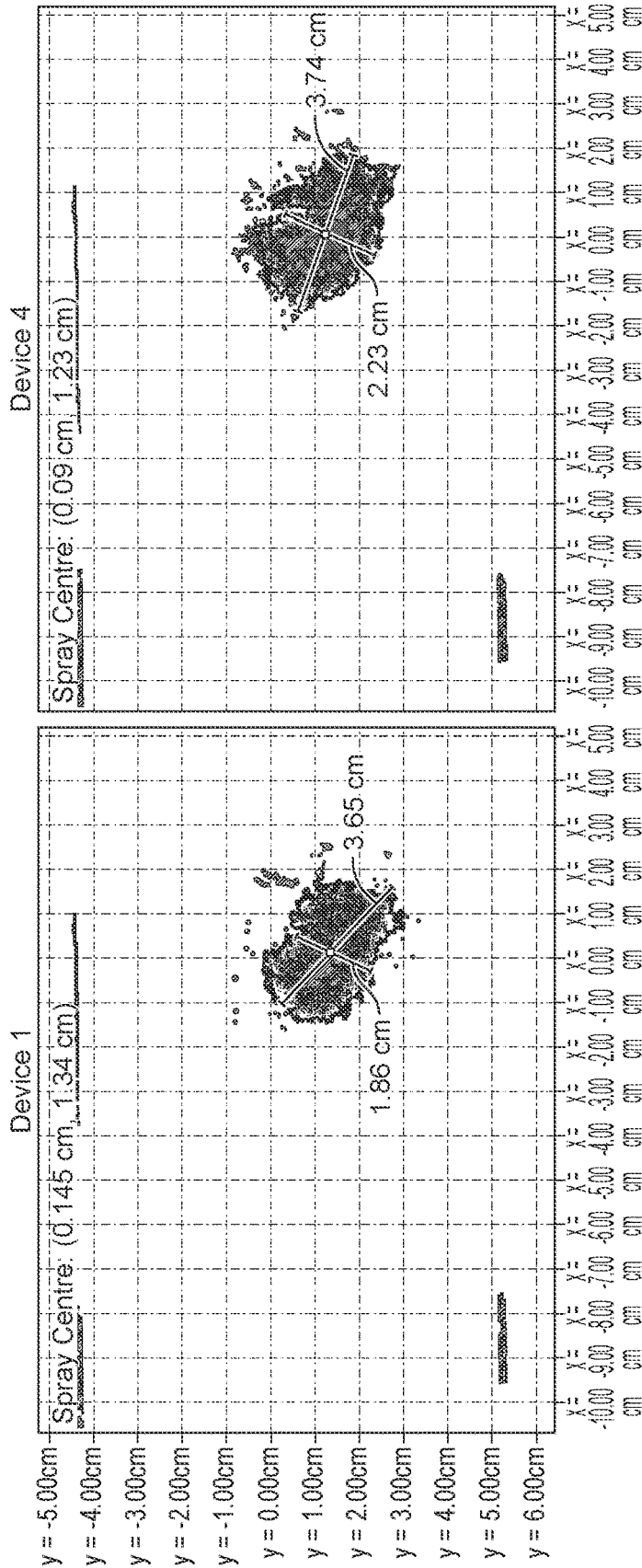
FIG. 13A and 13B show the results of spray pattern testing.
Figure 13B:
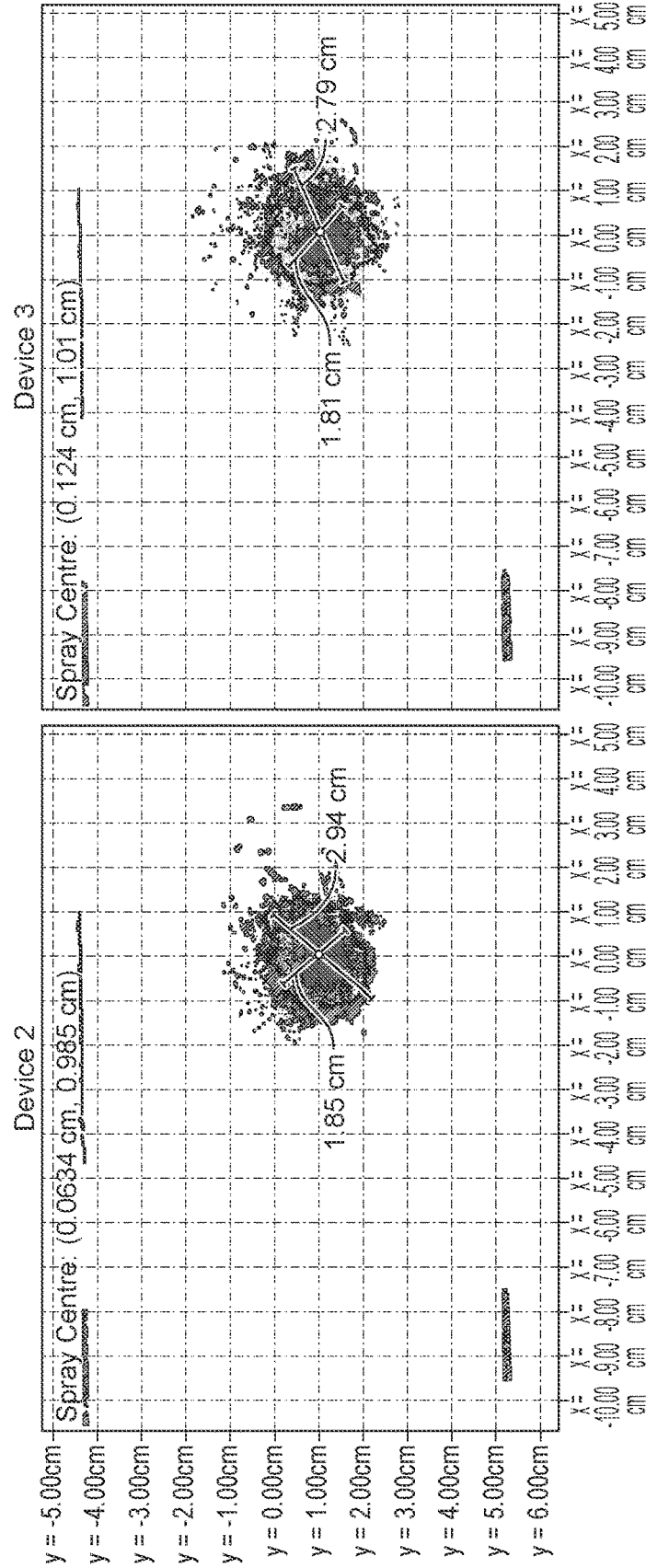

As shown in Table 1 and as also drawn in the graphs of FIGS. 11A to 11C, the high flow devices, which is to say those with mouthpiece regions with air bypass as described with reference to FIGS. 6 and 7 have a significantly more uniform recovery of Stages 4 and 5 (and other stages) by the NGI than the standard devices, Stages 4 and 5 being particularly useful therapeutic particle sizes.

For Stage 4 particles, the high flow devices achieved results at 2 kPa, 4 kPa and 6 kPa of 11.85, 13.38 and 14.72 mcg respectively, the highest of these figures only being 24% higher than the lowest, whereas the standard devices achieved equivalent results of 10.91, 14.61 and 16.46 mcg, of which the highest figure is 51% higher than the lowest. Therefore a more consistent delivery of Stage 4 particles is achieved by the high flow devices than the standard devices across this range of pressure drops applied.

Further, for Stage 5 particles, the high flow devices achieved results at 2 kPa, 4 kPa and 6 kPa of 12.28, 11.39 and 10.79 mcg respectively, the highest of these figures only being 14% higher than the lowest, whereas the standard devices achieved equivalent results of 17.44, 15.31 and 14.41 mcg, of which the highest figure is 21% higher than the lowest. Therefore a more consistent delivery of Stage 5 particles is achieved by the high flow devices then the standard devices across this range of pressure drops applied.

Plume Geometry and Spray Pattern

Using a high-speed camera operating at 500 Hz to capture images of the formulation particles from the same types of high flow and standard devices moving through the light-sheet formed by a FireFLY laser provided by Oxford Lasers, with lighting planes along (vertical) and perpendicular (also vertical) to the direction of expected exit flow (i.e. perpendicular to mouthpiece exit/circumferential flange 206), the captured images were processed by the application software, Oxford Lasers Envision Patternate, to provide detailed data on the plume geometry & spray pattern from the device. The software can be purchased from Oxford Lasers.

The air flow rate respective to each device type was when a pressure drop of 4 kPa was applied to the respective mouthpiece, the flow rates resulting from this being about 60 l/min for standard devices and about 85 l/min for high flow devices.

The results are shown in FIGS. 12A, 12B, 13A and 13B, and Tables 2 through 5 below. Advantageously, the high flow devices of the present disclosure have a narrower plume cone angle at 33.52 degrees on average than the 35.72 degrees of the standard inhalers; the plume is also straighter out of the high flow devices' mouthpieces, advantageously at an angle measured of 97.73 degrees on average (from the plane of the mouthpiece exit), instead of 104.96 degrees with standard devices. The spray pattern also at a distance of 3 cm from the mouthpiece exit had a smaller spray pattern area on average at 4.51 $cm^2$ instead of 6.16 $cm^2$ with the standard devices. Furthermore, the ratio at the same 3 cm plane of maximum to minimum plume cross-dimension was for high flow devices on average 1.55, which is smaller than the 1.87 demonstrated by the standard devices, the spray pattern therefore advantageously being more compact or rounder and likely to be more effective. As shown in these figures, the spray pattern has denser spray near and at a centre of the plume than near or at a peripheral edge of the plume.

TABLE 2

Spray geometry test results for standard inhaler

| | Plume Angle/Orientation) (°) | Cone Angle (°) | Cone width (cm) at 3 cm from mouthpiece | Length (cm) |
|---|---|---|---|---|
| Average | 104.96 | 35.72 | 1.57 | 10.65 |
| SD | 0.71 | 1.85 | 0.2 | 0.66 |

TABLE 3

Spray geometry test results for the high-flow inhaler

| | Plume Angle/Orientation (°) | Cone Angle (°) | Cone width (cm) at 3 cm from mouthpiece | Length (cm) |
|---|---|---|---|---|
| Average | 97.73 | 33.52 | 1.41 | 11.18 |
| SD | 1.91 | 1.94 | 0.08 | 0.17 |

TABLE 4

Spray pattern test results for standard inhaler

| | Length of shortest diameter (cm) | Orientation of shortest diameter (°) | Length of longest diameter (cm) | Orientation of longest diameter (°) | Min/ max ratio | Area (cm$^2$) |
|---|---|---|---|---|---|---|
| Average | 2 | 62.02 | 3.72 | 37.08 | 1.87 | 6.16 |
| SD | 0.22 | 11.76 | 0.25 | 10.25 | 0.22 | 0.54 |

TABLE 5

Spray pattern test results for high-flow inhaler

| | Length of shortest diameter (cm) | Orientation of shortest diameter (°) | Length of longest diameter (cm) | Orientation of longest diameter (°) | Min/ max ratio | Area (cm$^2$) |
|---|---|---|---|---|---|---|
| Average | 1.93 | 59.78 | 2.97 | 31.03 | 1.55 | 4.51 |
| SD | 0.21 | 15.56 | 0.17 | 14.98 | 0.08 | 0.59 |

Typically, the dry powder medicament used in the breath-actuated dry powder inhaler comprises a medicament active selected from the group consisting of anti-inflammatory agents, anti-cholinergic agents, $\beta_2$-adrenoreceptor agonists, anti-infective agents, anti-histamines and combinations thereof.

Suitable anti-inflammatory agents include corticosteroids and NSAIDs. Suitable corticosteroids which may be used include those oral and inhaled corticosteroids and their pro-drugs which have anti-inflammatory activity. Examples include methyl prednisolone, prednisolone, dexamethasone, fluticasone propionate, 6a, 9a-difluoro-17a-[(2-furanylcarbonyl) oxy]-11-hydroxy-16a-methyl-3-oxo-androsta-1, 4-diene-17-carbothioicacid S-fluoromethyl ester, 6a, 9a-difluoro-11-hydroxy-16a-methyl-3-oxo-17a-propionyloxy-androsta-1, 4-diene-17p-carbothioic acid S-(2-oxo-tetra-hydro-furan-3S-yi) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6a, 9c-difluoro-11-hydroxy-16a-methyl-17a-[(4-methyl-1,3-thiazole-5-carbonyl)oxy]-3-oxo-androsta-1,4-diene-17,8-carbothioic acid S-fluoromethyl ester and 6a, 9a-difluoro-17a-[(2-furanylcarbonyl)oxyl-11-hydroxy-16a-methyl-3-oxo-androsta-1,4-diene-17p-carbothioic acid S-fluoromethyl ester, more preferably 6a, 9a-difluoro-17a-[(2-furanylcarbonyl)oxy]-11-hydroxy-16a-methyl-3-oxo-androsta-1,4-diene-17-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis.

Suitable other ($\beta$2-adrenoreceptor agonists include salmeterol (e.g. as the xinafoate), salbutamol (e.g. as the sulphate or the free base), formoterol (e.g. as the fumarate), fenoterof or terbutaline and salts thereof.

Suitable anticholinergic agents are those compounds that act as antagonists at the muscarinic receptor, in particular those compounds, which are antagonists of the M1 and M2 receptors. Compounds include the alkaloid of the belladonna plants as illustrated by the likes of atropine, scopolamine, homatropine, hyoscyamine; these compounds are normally administered as a salt, being tertiary amines.

Particularly suitable anticholinergics include ipratropium (e.g. as the bromide), sold under the name Atrovent, oxitropium (e.g. as the bromide), glycopyrrolate (e.g. as the bromide), and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-34856-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118.

Suitable antihistamines (also referred to as H1-receptor antagonists) include any one or more of the numerous antagonists known which inhibit H1-receptors, and are safe for human use. All are reversible, competitive inhibitors of the interaction of histamine with H1-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine.

Exemplary antagonists are as follows:Ethanolamines:carbinoxamine maleat, clemastine fumarate, diphenylhydramine hydrochloride, and dimenhydrinate.

Ethylenediamines:pyrilamine amleate, tripelennamine HCl, and tripelennamine citrate.

Alkylamines:chlropheniramine and its salts such as the maleate salt, and acrivastine.

Piperazines:hydroxyzine HCl, hydroxyzine pamoate, cyclizine HCl, cyclizine lactate, meclizine HCl, and cetirizine HCl.

Piperidines:Astemizole, levocabastine HCl, loratadine or its descarboethoxy analogue, and terfenadine and fexofenadine hydrochloride or another pharmaceutical acceptable salt.

Azelastine hydrochloride is yet another H1 receptor antagonist which may be used in combination with a PDE4 inhibitor.

Particularly suitable anti-histamines include methapyrilene and loratadine.

Generally, powdered medicament particles suitable for delivery to the bronchial or alveolar region of the lung have a mass median aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (e.g. starch, cellulose and the like), lactose, glucose, mannitol, amino acids, and maltodextrins, and inorganic excipients such as calcium carbonate or sodium chloride. Lactose is a preferred excipient.

Particles of powdered medicament and/or excipient may be produced by conventional techniques, for example by micronisation, milling or sieving.

Additionally, medicament and/or excipient powders may be engineered with particular densities, size ranges, or characteristics. Particles may comprise active agents, surfactants, wall forming materials, or other components considered desirable by those of ordinary skill.

The invention claimed is:

1. An inhaler for the inhalation of powder medication, the inhaler having an inhaler body and at least one reservoir containing powder medication, the inhaler body defining an air inlet for allowing air to enter the inhaler body and an outlet for transmission to a patient of air entering the inhaler body through the air inlet and powder medication, the outlet having a total cross-sectional area for flow which is more than 80% and less than 100% of a total cross-sectional area of the air inlet, the outlet comprising a primary outlet for transmitting dry powder medicament entrained in air and at least one secondary outlet for transmitting a bypass flow of air alone without medicament, the inhaler further comprising a deagglomerator, located within the inhaler body, the deagglomerator including a swirl chamber, at least one swirl chamber inlet port for transmitting air without powder medicament, and a single swirl chamber medicament inlet for transmitting air with powder medicament, wherein the air inlet defined by the inhaler body is a sole air inlet shared by all of the primary outlet, the at least one secondary outlet, the at least one swirl chamber inlet port for transmitting air without powder medicament, and the swirl chamber medicament inlet for transmitting air with powder medicament, and wherein a single delivery passageway leads from the air inlet of the inhaler to the swirl chamber medicament inlet of the deagglomerator.

2. The inhaler of claim 1 in which the total cross-sectional area of the outlet is more than 85% and less than 100% of the total cross-sectional area of the air inlet.

3. The inhaler of claim 1 in which the primary outlet is substantially circular.

4. The inhaler of claim 1 in which the primary outlet has a cross-sectional area of 30 to 50 $mm^2$.

5. The inhaler of claim 4 in which the total cross-sectional area of all said secondary outlets is 5 to 15 $mm^2$.

6. The inhaler of claim 1 in which the air inlet is generally elliptical in shape and has at least an upper or lower edge portion thereof which is elliptical.

7. The inhaler of claim 1, wherein an area of flow through the at least one swirl chamber inlet port combined with the swirl chamber medicament inlet defines a combined cross-sectional area which is less than the total cross-sectional area of the air inlet to the body.

8. The inhaler of claim 7 in which the combined cross-sectional area is 3 to 5 times larger than the total cross-sectional area of all said secondary outlets.

9. The inhaler of claim 1 in which a cone angle of a plume of substance emitted from the inhaler is less than 35 degrees.

10. The inhaler of claim 1 in which a cross sectional area at a distance 3 cm away from the outlet of a plume of substance emitted from the inhaler is less than 6 $cm^2$.

11. The inhaler of claim 1 in which at a distance 3 cm away from the outlet, a ratio of maximum to minimum cross-dimensions of a plume of substance emitted from the inhaler is less than 1.8.

12. The inhaler of claim 1 comprising a dry powder medicament.

13. The inhaler of claim 1 in which the air inlet, the primary outlet and the at least one secondary outlet are configured such that delivery of Stage 4 particles in a Copley Scientific Next Generation Impactor test at pressure drops of 2 kPa, 4 kPa and 6 kPa varies between a most weight of particles and least weight of particles and the most weight of particles is less than 50% more than the least weight.

14. The inhaler of claim 1 in which the primary and the at least one secondary outlets are configured such that delivery of Stage 5 particles in a Copley Scientific Next Generation Impactor test at pressure drops of 2 kPa, 4 kPa and 6 kPa varies between a most weight of particles and least weight of particles and the most weight of particles is less than 20% more than the least weight.

15. A method of treating a respiratory disease or disorder comprising actuating the inhaler of claim 1 to administer a therapeutically effective amount of one or more active ingredients.

16. The method of claim 15, wherein the inhaler is a dry powder inhaler and the step of actuating the inhaler comprises inhaling through the inhaler.

17. The method of claim 15, wherein the respiratory disease or disorder is one or more of asthma and/or chronic obstructive pulmonary disease.

18. The method of claim 15, wherein the one or more active ingredients includes one or more of budesonide, formoterol fumarate, albuterol, salbutamol sulphate, fluticasone propionate and salmeterol, and/or fluticasone propionate and salmeterol xinafoate.

19. An inhaler for the inhalation of powder medication, the inhaler having an inhaler body and at least one reservoir containing powder medication, the inhaler body defining an air inlet and an outlet for transmission to a patient of air entering the inhaler body through the air inlet and powder medication, the outlet comprising a primary outlet for transmitting dry powder medicament entrained in air and at least one secondary outlet for transmitting a bypass flow of air, the inhaler further comprising a deagglomerator, located within the inhaler body, the deagglomerator including a swirl chamber, at least one swirl chamber inlet port for transmitting air without powder medicament, and a single swirl chamber medicament inlet for transmitting air with powder medicament, wherein the air inlet defined by the inhaler body is a sole air inlet shared by all of the primary outlet, the at least one secondary outlet, the at least one swirl chamber inlet port for transmitting air without powder medicament, and the swirl chamber medicament inlet for transmitting air with powder medicament, wherein a single delivery passageway leads from the air inlet of the inhaler to the swirl chamber medicament inlet of the deagglomerator, and wherein the primary and secondary outlets being configured to produce a plume of particulate substance emitted from the inhaler, said plume having one or more of a cone angle of the plume which is less than 35 degrees, a plume angle of from about 95 degrees to about 100 degrees, and/or, at a plane 3 cm away from the outlet, a cross sectional area which is less than 6 cm$^2$ or has a ratio of maximum to minimum cross-dimensions which is less than 1.8.

\* \* \* \* \*